United States Patent
Grae

[11] Patent Number: 5,914,255
[45] Date of Patent: Jun. 22, 1999

[54] TEMPERATURE SHOCK METHOD AND APPARATUS

[76] Inventor: Joel B. Grae, 4 Top of the Ridge, Mamaroneck, N.Y. 10543

[21] Appl. No.: 08/812,110

[22] Filed: Mar. 5, 1997

Related U.S. Application Data

[60] Provisional application No. 60/017,121, Mar. 6, 1997.

[51] Int. Cl.$^6$ .............. C12N 13/00; A61L 2/00; A23C 3/07; A23L 3/16; A61F 2/00
[52] U.S. Cl. .............. 435/173.1; 422/21; 422/38; 426/237; 426/521; 607/100; 607/101
[58] Field of Search .............. 422/21, 38; 426/237, 426/521; 607/100, 101; 435/173.1

[56] References Cited

U.S. PATENT DOCUMENTS

| | | | |
|---|---|---|---|
| Re. 32,695 | 6/1988 | Nahra et al. | 261/118 |
| 1,522,188 | 1/1925 | Hull | 392/312 |
| 1,522,386 | 1/1925 | Parsons et al. | 99/453 |
| 2,550,584 | 4/1951 | Mittelmann | 99/451 |
| 3,041,958 | 7/1962 | Abrams | 99/453 |
| 3,113,872 | 12/1963 | Jones | 426/511 |
| 3,156,176 | 11/1964 | Wakeman | 99/453 |
| 3,182,975 | 5/1965 | Stewart | 261/34.1 |
| 3,450,022 | 6/1969 | Engel | 99/453 |
| 3,451,327 | 6/1969 | Nelson | 99/453 |
| 3,934,042 | 1/1976 | De Stoutz | 426/248 |
| 4,160,002 | 7/1979 | Janivtchik | 261/76 |
| 4,161,909 | 7/1979 | Wakeman | 99/453 |
| 4,591,463 | 5/1986 | Nahra | 261/116 |
| 4,737,364 | 4/1988 | Kalogris | 424/195.1 |
| 4,776,268 | 10/1988 | Bronnert | 99/453 |
| 4,787,304 | 11/1988 | Bronnert | 99/453 |
| 4,923,855 | 5/1990 | Jensen | 514/188 |
| 4,954,492 | 9/1990 | Jensen | 514/188 |
| 4,957,760 | 9/1990 | Swartzel et al. | 426/399 |
| 4,975,246 | 12/1990 | Charm | 422/21 |
| 5,209,157 | 5/1993 | Sanchez Rodriguez | 99/455 |
| 5,235,905 | 8/1993 | Bushnell et al. | 99/451 |
| 5,294,606 | 3/1994 | Hastings | 514/53 |
| 5,389,335 | 2/1995 | Charm et al. | 422/21 |
| 5,539,673 | 7/1996 | Charm et al. | 364/557 |

FOREIGN PATENT DOCUMENTS 2052967   1/1996   Russian Federation .

OTHER PUBLICATIONS

Sugihara, T.F., "Heat Pasteurization of Liquid Whole Egg," *Food Technology*, (Aug. 1966): 100–107.

Zhang Qinghua, "Engineering Aspects of Pulsed Electric Field Pasteurization", *Journal of Food Engineering* (1995): 261–281.

Heimburg et al. (1994) Biochemistry, 33(32), "Thermotropic Behavior of Dimyristoylphosphatidylglycerol and Its Interaction with Cytochrome C", pp. 9477–9488.

*Primary Examiner*—Jon P. Weber
*Attorney, Agent, or Firm*—Milde, Hoffberg & Macklin, LLP

[57] ABSTRACT

A method for treating a biological organism in a medium, comprising heating the medium containing the organism by a temperature of at least about 2° C. at a rate which exceeds a relaxation rate of a cellular membrane of that organism, under such time and temperature conditions which do not thermally denature a substantial portion of the biological proteins.

23 Claims, 13 Drawing Sheets

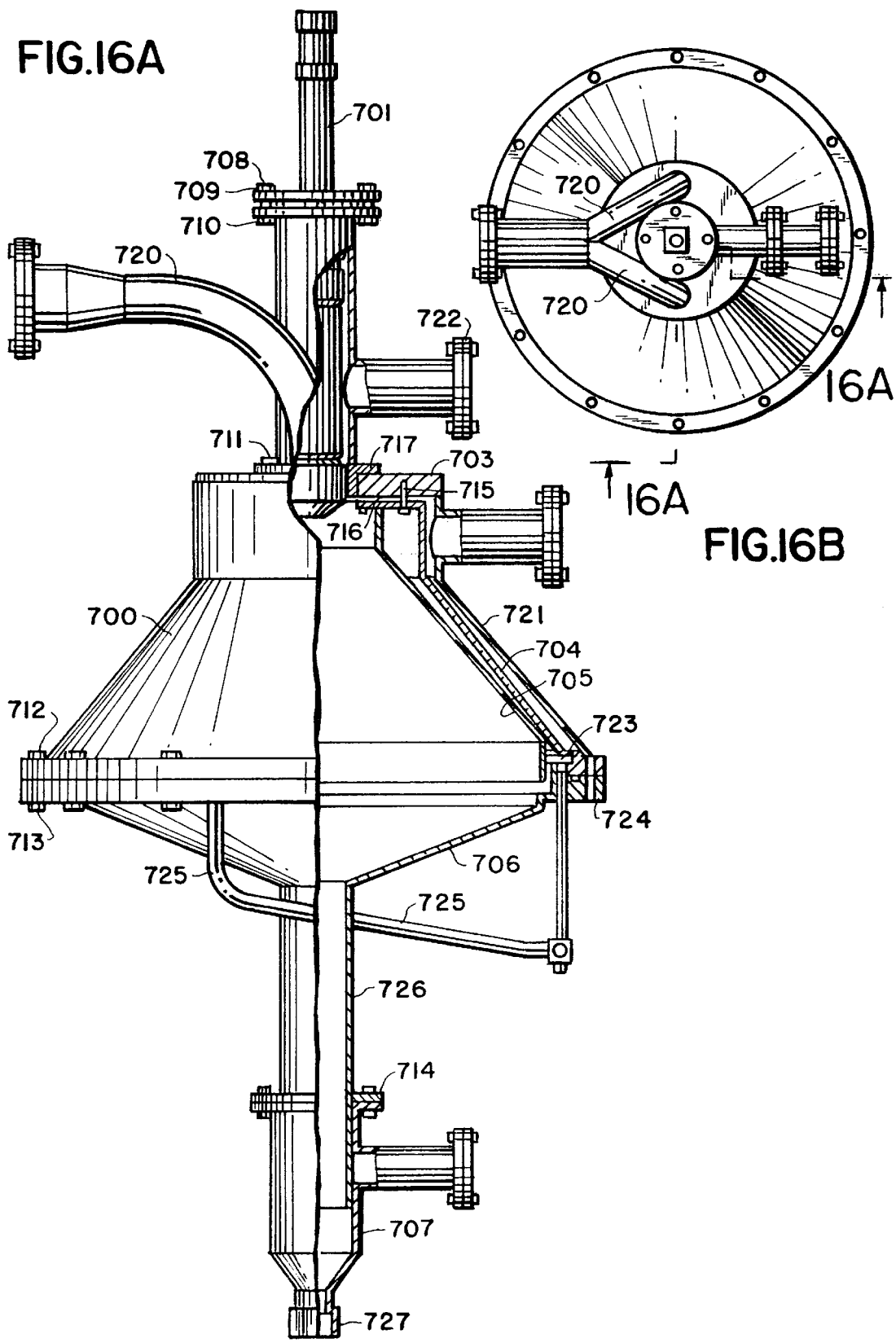

TEMPERATURE SHOCK METHOD AND APPARATUS

This application claims benefit of USC Provisional Appln. 60/017,121 filed Mar. 6, 1997.

FIELD OF THE INVENTION

The present invention relates to the field of methods and systems for altering cells or tissues of organisms with high rate thermal changes. These alterations are useful for developing medicines and for medical treatments.

BACKGROUND OF THE INVENTION

A number of methods are known for reducing bacterial activity in liquids. Traditionally, a so-called "Pasteurization" process is employed, which operates by the principles of thermal denaturation of proteins to inactivate bacteria. Thus, the liquid is raised to a particular temperature for a proscribed duration, to effect a statistical reduction in the number of or even elimination of all viable bacteria. In an effort to reduce a duration of the process, high temperatures may be employed, which raise the temperature of the fluid to, e.g., 150° C. for 2–4 seconds under pressure, followed by a flashing (rapid boiling) to lower the temperature, thus limiting the duration of the treatment. Such systems thus require a very high temperature, and may alter a taste of a potable liquid or food product, such as is the case with milk. Depending on how the heat is applied, precipitation of proteins in the product or other physical changes may occur. In addition, the presence of oxygen during treatment may cause accelerated oxidation.

The most widely used Pasteurized technique involves subjecting food products to heat treatment as high as 65–75° C. and exposing same to this temperature for a period of time of 30 minutes. This is the so-called long-term heat treatment. The second technique involves subjecting food products to heat treatment at a temperature of 70–75° C. and exposing same to this temperature for a period of time of 2–4. minutes. The third technique involves subject food products to short term heat treatment at a temperature of 95° C. and exposing same to this temperature for 30 seconds. The fourth technique includes ultra high temperature heat treatment. It involves subjecting food products to a temperature of 110–140° C. and exposing same to this temperature for a period of time of 2–3 seconds. These treatment are thus based on a thermostability time-temperature relationship of microorganisms. Thermostable life-time is defined as a life-time of microorganisms at a given temperature. The higher the temperature, the shorter the thermostable period. An effective Pasteurization treatment thus subjects food products to heat treatment at a certain temperature for a period of time which is longer than the thermostable period.

These prior art techniques are generally directed toward the thermal denaturation of essential cell elements, they effectively cook the food product, including any biological organisms therewithin. Thus, in addition to altering the taste of the food product, they also affect its composition, for example vitamin concentrations, and structure, for example coagulating proteins or producing sediments. These sediments also necessitate regular cleaning of the system, especially any higher temperature portions, such as heat exchange surfaces.

Some of these drawbacks can be avoided by using the direct heat treatment, which heats the product by way of direct contact of the product subjected to Pasteurization with the heating medium, for instance, steam, rather than through a heat transferring surface of heat exchange equipment. This method eliminates release of the milk "stone" in the heating zone and lessens its appearance on other surfaces of the equipment. These known methods transfer the product into the Pasteurizer, and inject steam made from potable water to a desired temperature, for a desired period. The product is cooled and excess water from condensed steam eliminated. This technique allows a relatively quick heat treatment of the product, and has been found of particular use in ultra high temperature heat treatments. The technique avoids exposure to temperatures higher than a desired final temperature, and thus may limit sedimentation, which may appear, for example, as milk "stone" in a Pasteurization process. Where direct steam contact is used, it dilutes the medium, for example up to 30% of the product mass, with an ultra-high temperature Pasteurization technique, which subsequently is often removed.

These known methods of Pasteurization strive to maintain laminar flow of milk during the process, and thus do not atomize the milk. As a result, these systems fail to raise the temperature of the bulk of the milk at a rapid rate, and rather gradually raise the bulk temperature to the Pasteurization temperature, at which the milk is maintained for the desired period. Of course, a small surface layer may experience rapid temperature rises.

Zhang, et al., "Engineering Aspects of Pulsed Electric Field Pasteurization", Elsevier Publishing Co. (1994) 0260-8774(94)00030-1, pp. 261–281, incorporated herein by reference, relates to Pulsed Electric Field Pasteurization, a non-thermal Pasteurization method. This method (as well as other biological treatment methods) may be combined with other methods, to enhance efficacy of the composite process, while avoiding the limitations of an excess exposure to any one process.

PRIOR ART

RU 2,052,967 (C1) relates to a rapid temperature rise bactericidal treatment method.

Abrams et al, U.S. Pat. No. 3,041,958 relates to a steam processing temperature control apparatus. Wakeman, U.S. Pat. No. 3,156,176 relates to a steam Pasteurization system. Stewart, U.S. Pat. No. 3,182,975 relates to a steam injection heater, which employs impeller blades to mix steam and milk for rapid heating. Engel, U.S. Pat. No. 3,450,022 relates to a steam infuser for high temperature steam treatment of liquids. Nelson, U.S. Pat. No. 3,451,327 relates to a steam injector for a milk sterilizer. This device is intended to bring the milk to a high temperature, and thus allows thermal communication between the steam and milk prior to venting. De Stoutz, U.S. Pat. No. 3,934,042 relates to a system for treating beverages, including milk, beer, wine and fruit juices, for sterilization or Pasteurization. The liquid is held at elevated temperatures for extended periods. Janivtchik, U.S. Pat. No. 4,160,002 relates to steam injectors for Pasteurizing milk using pressurized steam. Wakeman, U.S. Pat. No. 4,161,909 relates to an ultrahigh temperature heating system for heating, e.g., milk. The milk falls in a curtain configuration in a steam chamber. The milk is held at a high temperature after heating. Nahra et al. U.S. Pat. No. 4,591,463, and Nahra et al. Re. 32,695, incorporated herein by reference, relate to a milk ultra Pasteurization apparatus in which sheets of milk fall within a steam filled chamber for ultra high temperature Pasteurization. Bronnert, U.S. Pat. Nos. 4,787,304 and 4,776,268 relate to an infusion heating apparatus for sterilizing liquid food products, having a porous steam dispensing cylinder or diffuser located along a central axis of a treatment vessel. Sanchez Rodriguez, U.S. Pat. No. 5,209,157 relates to a dairy preparation system which involves an ultrahigh temperature treatment step.

SUMMARY AND OBJECTS OF THE INVENTION

The present invention seeks to alter cell characteristics by a thermal shock process, which may be used, for example, to inactivate or kill bacteria, alter cell surface chemistry or antigenicity, disrupt membranes, activate cell functions or responses, disaggregate cells, as a pretreatment before cell fusion or infection, activate or change the function of a cellular parasite (bacteria, mycoplasma, virus, prion, etc.), affect mitochondrial functioning or the functioning of other organelles. On an organism level, the present invention may be used to treat bacterial infections, such as osteomyelitis, viral infections such as AIDS, human or animal Herpes viruses (including HHV-5 and EBV, as well as CMV, HSV-1, HSV-2, VZV, HHV-8,and the like), treat cancer, sarcoma, mesothelioma, teratoma or other malignancy or neoplasm, treat skin conditions, such as psoriasis, treat inflammation, treat fungal diseases, blood borne diseases, leukemias and the like. The present invention may also have utility in the treatment of syndromes, which may be multifactorial in origin and involve an immunological component or defect. Therefore, the present invention may also find utility in the treatment of chronic fatigue syndrome (CFS), for example by applying immune stimulation therapy through treatment of blood or blood components.

The broad utility of the present invention comes from its ability to carefully control a stress applied to a cell. This stress may, of course, kill the cell or selectively kill a subpopulation of cells, but more importantly, it is believed that the present invention may be applied to cells to have a measurable non-transient effect which does not immediately result in cell death. In this manner, the present method provides a new manipulation modality for cells.

In contrast to known cellular thermal inactivation methods, the present invention does not rely on thermal denaturation of cellular proteins and enzymes, but rather on a rapid temperature rise which irreversibly changes the cell, at temperatures and energy levels below those required by traditional Pasteurization processes.

In particular, the system and method according to the present invention treat a product such that the temperature of a medium in which all or a portion of the cells exist rises at such a rapid rate that normal accommodation mechanisms, which might allow the cell to avoid permanent effect from a slower temperature rise rate treatment, are unavailable or ineffective. Thus, it is an aspect of the present invention to alter cell functioning based on a rate of temperature change during treatment, rather than based on a time-temperature product function or a maximum temperature.

The present invention is thus believed to operate by a physical principle different than thermal denaturation, the principle behind Pasteurization. Rather than a thermal denaturation of the proteins, as well as proteins which may be in the extracellular medium, the present invention operates by thermal shock, which is believed to disrupt or alter membrane structures or membrane components of cells. Typical extracellular medium fluids include milk, egg white, blood plasma, cell culture medium, fermentation broth, fruit juices, and the like Thus, rather than a high temperature, per se, the present invention requires a high rate of temperature rise. The resulting maximum temperature may be limited to temperatures which do not denature various proteins, e.g., a maximum temperature of 0–75° C. It is clear, therefore, that the maximum temperature may remain sub-physiological, or rise to relatively high levels. For food processing, the maximum temperatures will often be on the higher end of the scale, in the 40–75° C. range, while in medical or pharmaceutical process, the maximum temperatures will often be in the middle of the range, e.g., 15–45° C.

There are a number of slightly different theories why thermal shock may affect cells, or more particularly membranes, membrane bound cell structures or organelles. When the thermal shock is substantial, bacterial or spore killing is effected. Under gentler conditions, organisms may survive, giving rise to the possibility of non-lethal cellular treatments.

One theory of operation of the present invention relates to the glass transition temperature of membrane structures. Cellular membranes are generally formed of phospholipid bilayers with proteins, lipoproteins and glycoproteins inserted on the inside, outside, or protruding through the membrane. The membrane, especially the fatty acid chains of the phospholipids, are physiologically maintained in a fluid condition, and thus lipids and proteins are motile across the surface of the membrane. For example, under comparable circumstances, a lipid molecule may travel at a rate of about 2 microns per second, with proteins traveling at a rate of several microns per minute, in the plane of the membrane. Membrane components, though mobile in the plane of the membrane, are generally slow to switch or invert between the outer and inner surface. For example, transverse diffusion rate of phospholipids is about $10^{-9}$ the rate of lateral diffusion, for a typical 50Å distance (the thickness of a phospholipid bilayer membrane). The viscosity of a cell membrane typically is about 100 times that of water.

On the other hand, the membrane structures of living cells have some long-term ordering of molecules, especially the structures on the surface of the membrane (as opposed to the lipid phase in the middle of the membrane), and therefore are in this sense crystalline. Thus, the phrase "liquid crystal" is apt for the composite structure. Among other functions, the controlled membrane fluidity is believed to be necessary for various mediated transport systems which involve the movement of carriers within or through the membrane. The membrane proteins also have, in their natural state, a separation of charged and uncharged portions, allowing lipophilic portions of the proteins to be stably inserted into the membrane structure, with hydrophilic portions protruding extracellularly or intracellularly from the membrane, into the cytoplasm or extracellular fluid. Intracellular membranes may also have asymmetry. Since the phospholipids are essentially undistinguished, the long term (i.e., over distances of tens of Angstroms) ordering of the membrane along its surface is related to arrangements of the protein components and the polar end-groups of the phospholipids. Some of the proteins or protein structures which extend through the membrane provide channels which allow ions, such as sodium, potassium and chloride to readily cross, or to be selectively controlled or pumped. The size of the channel allows selectivity between differing ions, e.g., sodium and potassium.

The tertiary configuration of the proteins (the three dimensional structure of a single protein molecule), and quaternary configuration of peptide structures (the spatial interaction of separate molecules) are thus critical for proper protein insertion in the membrane, and protein functioning. Thus, the membrane is ordered, and this ordering relates to its function. A disruption of the ordering affects the cell function, and may destroy the cell, or have a lesser damaging, distinct or selective effect.

The membrane fluidity may be controlled by fatty acid composition. For example, bacteria use this mechanism. The fatty acyl chains of lipid molecules may exist in an ordered, crystal-like state or in a relatively disordered fluid state. The transition from the ordered to disordered state occurs when the temperature is raised above a "melting" temperature, or more properly, a glass transition temperature. In the case of fatty acyl chains within the membrane, the physiological state is fluidic. Of course, the membrane structure may have a number of different glass transition temperatures, for the various components and their respective energetically favorable orderings which may exist. This glass transition temperature depends on a number of factors, including the length of the fatty acyl side chain and their degree of unsaturation. Unsaturation (with the naturally occurring cis-oriented carbon-carbon bonds) causes "kinks" in the side chains, and increases bond rotation on either side of the unsaturation, both of which impair orderly packing, thus reducing crystallinity and increasing the glass transition temperature. Long fatty acyl chains interact more strongly, stabilizing the structure, and in increase in their proportion leads to a decrease in glass transition temperature.

It is known that in *E. coli*, the ratio of saturated to unsaturated fatty acyl chains in the cell membrane decreases from 1.6 to 1.0 as the temperature decreases from 42° C. to 27° C. This decrease in the proportion of saturated residues is believed to prevent the membrane from becoming too rigid at lower temperatures. Higher species, including mammals, regulate cell membrane fluidity through cholesterol content, although this mechanism is believed to be absent in bacteria. It is believed that these membrane-composition accommodation mechanisms are comparatively slow.

It is also believed that organisms, such as bacteria, maintain their cell membranes a number of degrees below an important glass transition temperature of the membrane. thus assuring a balance between membrane fluidity and crystalline-like ordering. This crystalline state also implies a non-linear response of the membrane to temperature variations around the glass transition temperature.

Cellular mechanisms are believed to be present which assure that, through commonly encountered temperature variations, irreversible cellular damage does not occur. Some of these mechanisms are active or controlled, and thus have a latency. Some of these temperature changes may also trigger physiological cellular responses, such as so-called temperature shock proteins. Some of these mechanisms are physical and passive, and thus occur relatively rapidly. These include stretching, membrane shape changes, and the like.

According to this theory, the system and method according to the present invention seek to take advantage of these delayed responses in the accommodation mechanisms to temperature increases, by increasing the temperature, through this glass transition temperature, at such a rate that the cellular mechanisms do not have a chance to effectively respond, thus allowing irreversible damage to the bacteria, presumably through a disruption of the higher levels of organization, without necessarily affecting the lower organizational levels of structure. Thus, the temperature of the bacteria need not be raised to a temperature sufficient to thermally denature the tertiary structure of proteins.

Another theory for the observed bactericidal effect, and indeed the sterilizing effect believed to exist, is that, though the temperature of the cells is raised, it is not raised sufficiently to completely fluidize the membranes, leaving them comparatively stiff, brittle or non-compliant. The thermal shock according to the present invention also produces a mechanical stress, which may damage or affect the membrane. This damage may result in lysis, or a less severe mechanical disruption, which may later result in cell death or other response. This mechanical stress may also activate cellular processes or otherwise influence cell functioning. This effect is essentially opposite to that seen in high temperature Pasteurization (HTP), wherein the sustained higher temperatures tend to liquefy the membrane; although these HTP processes are specifically intended to thermally denature proteins to inactivate cells.

High temperature change rates are needed in order to prevent the relaxation of structural changes in a cell, e.g., the cellular membrane, which occur over approximately 10–100 mS. With temperature rise rates in excess of this rate, an effect occurs, which may, for example, disrupt or inactivate bacteria or cells or have other effects.

The induced thermal shock thus produces a number of effects on the cell. First, the cell rapidly expands due to the increase in temperature. Second, the cellular membranes may experience a configurational change either as a primary effect or secondarily due to a phase, volume or shape change of cellular components. Third, while thermal denaturation generally is directed to essentially irreversible changes in the tertiary protein structures of critical proteins and enzymes, thermal shock may effectively reduce quaternary organization to control or alter the cell. Microtubule structures and nucleic acid conformations may also be affected.

According to the present invention, one method for inducing this controlled yet rapid temperature rise is by treating medium containing the cells, generally in relatively small droplets to provide a large surface area to volume ratio and small thermal inertia, held at a starting temperature, with an excess of steam at the desired final temperature. The interaction between the droplets and steam is rapid, equilibrating within milliseconds at the final temperature, with only a small amount of dilution due to the high latent heat of vaporization of steam. Generally, in order to reduce a rate-limiting boundary layer, the droplets are degassed prior to treatment.

The water derived from condensed steam chemically dilutes the droplets, rather than mechanically diluting them. In the case of milk, this means that the water is associated with the milk proteins, and the treatment does not substantially adversely affect the flavor of the milk. This excess water may also be removed. In the case of biological media, the dilution is relatively small, and therefore is unlikely to induce a hypotonic shock. However, to the extent that this hypotonic shock does induce a response, that response forms a part of the present invention.

Alternately, other controlled addition of energy to the cell-containing medium or tissue may be used. Thus, for treatment of human organs, a powerful microwave device may be used, which heats the aqueous phase of the tissue. The energy of the microwave is controlled so that the tissues are heated to a desired temperature. The energy is applied rapidly, in order to obtain the desired temperature rise rate, e.g., in excess of 1000° C. per second, over a short period, which also means that thermal diffusion or blood perfusion become comparatively insignificant factors in the treatment. The volume to be treated may be physically measured, estimated, or empirically determined by a "test" treatment which applies a relatively small amount of energy and determines the temperature rise in response. In any case, it is important to assure uniformity of treatment of bulk tissues, in order to prevent spatial variations in treatment. However, where the goal is not treatment of all cells within the organ or tissue, for example and organ such as lung, liver or brain, or a tissue such as a solid tumor, then the treatment may be directed toward a portion of the tissue, with care taken not to over-treat any essential tissues. Thus, non-uniform or non-uniform fields of microwaves or infrared radiation (coherent or incoherent, monochromatic or broadband) may be employed to heat cells or tissues.

In general, visible or ionizing radiation and acoustic waves are not preferred energy sources because, in order to raise the temperature by the desired amount, other effects will likely be produced in the tissues. However, where these other effects are desired or complementary, they may be employed.

A composite treatment may also be fashioned, in which a core tissue is destroyed, while a peripheral shell is partially treated. It is known that one mechanism by which neoplastic cells escape normal immunological surveillance is by hiding antigenic factors from the cell surface, or even not producing certain antigenic markers. It is believed that the present invention will overcome these mechanisms are disrupt or alter membranes so that antigenic markers or elements are accessible. In this case, cell death is not necessary for efficacy, as the mere presentation of unique or characteristic antigens may be sufficient to spur an immunologic response which results in an effective treatment.

Blood presents certain interesting properties material to its application for treatment according to the present invention. First, it may be transferred to an extracorporeal reactor. Second, blood components may be separated in real time, in a pheresis process, and individual blood components (erythrocytes, leukocytes, platelets, plasma, etc.) treated separately. Third, it is a liquid which maybe separated into small droplets. Thus, blood treatment may be effected through the "Pasteurizer" reactor, using treatment parameters which do not coagulate or denature blood proteins. Generally, a useful treatment does not attempt to kill all blood cells, or one would simply extravasate without reinfusion, or separate undesired cell components and not reinfuse undesired components.

Therefore, often a goal of therapy is either selective treatment of a subpopulation of the cells, or a non-lethal treatment applied non-selectively to all or some of the cells present. In order to effect a non-lethal treatment, the temperature rise rate is controlled, and/or the temperature rise and/or maximum temperature is controlled.

Blood treatments may be effective, for example, to treat CFS, AIDS, malaria, babesiosis, other viral, bacterial, fungal or parasitic diseases, leukemias or other blood-borne neoplasms, blood dysplasias and dyscrasias, immune disorders and syndromes. Bacterial-associated autoimmune mediated disorders, such as those related to spirochetes (syphilus, Lyme disease), as well as other autoimmune related diseases, such as rheumatoid arthritis and lupus, may also be subject to treatment according to the present invention.

In some syndromes, viruses play a primary or ancillary role. Many types of viruses have a lipid coat, which is, for example, derived from the cell membrane of a host cell before budding or lysis, generally with viral-specific proteins or glycoproteins. It is characteristic of chronic viral infections that the viruses avoid vigorous immunological response by not presenting antigenic proteins, or by mimicking host proteins. On the other hand, some chronic viral infections produce an autoimmune response which does not particularly target or eliminate viral infected cells. In either case, the temperature shock method according to the present invention allows relatively mild reconfiguration of membranes, allowing normally unavailable antigenic markers of membrane proteins or intracellular proteins to be presented to the host immune system. Thus, any disease which is characterized by deficient or misdirected host immunological response is a candidate for treatment according to the present invention. Accordingly, cells which are accessible through the blood, skin or in particular organs may be targeted with the temperature shock treatment.

It is also noted that temperature shock may be used to redirect the activities of a cell. For example, circulating immune cells may be refractory or hyperstimulated. A treatment according to the present invention may be used to "resynchronize" or reset cells to obtain a normal response. Thus, the present invention need not be directed to the treatment or destruction of abnormal cells, but rather to the use of temperature shock for a variety of purposes.

Since the treatment of an individual patient does not necessarily require high throughput, other energy sources may be used, besides steam and microwaves, including general infrared, laser, maser, and chemical sources. Therefore, for example, a stream of blood, or blood component(s), may be subjected to a controlled low power CO2 laser or microwave treatment to effect the temperature shock treatment. Further, using cell separation techniques, such as those developed by Coulter Electronics, Hialeah, Fla., individual blood cells may be individually treated, based on an identification of type, and then, for example, reinfused into the host.

The cell treatment methods according to the present invention may also be applied to in vitro techniques in order to control cells or select cell subpopulations. Typical applications include, for example, genetic engineering clonal selection for temperature shock resistance genes, which may be either a primary goal or a marker gene for a linked trait.

Another organ of interest is the skin, which may have tumors (malignant melanoma, basal cell carcinoma, etc.), psoriasis, viral, bacterial or fungal infection, inflammation, other immunological or autoimmune disorder, loss of elasticity, angioma, and other conditions. The skin is of particular interest because of the ease of external access to the surface. Therefore, for example, a stream of steam, laser beam or infrared source may be applied to the skin, in a manner which would quickly raise the temperature or the surface and possibly a region below the surface. In contrast to types of known treatments, the temperature rise is carefully controlled, while the heating is nearly instantaneous. The careful control is exerted, for example in the case of steam, by controlling the partial pressure of the steam and performing the treatment within a controlled environment, such as a hypobaric chamber or enclosure. In the case of laser, the pulse energy and repetition rate, as well as particular wavelength of the laser, e.g., $CO_2$ with 10.6 $\mu$m wavelength, may be empirically determined for an effective treatment. In the case of other electromagnetic waves, the field strength and duration of exposure are carefully controlled to effect a desired treatment.

Using a Pasteurization system according to the present invention, many log reductions in *E. coli* were achieved, for example a reduction of from $10^6$ per milliliter to the limit of detectability was achieved. Bacterial spores (*B. subtilis*) are also reduced, although possibly with lesser efficacy, for example a two log reduction (1% of original concentration) is achieved. It is believed that further refinement of the present system and method will prove more effective against these spores, and prove effective to kill or produce a response in various types of viruses, bacteria, fungi, protozoans, animal cells, and plant cells. The existence of organisms which survive treatment is clear evidence of the gentleness of treatment, and therefore that the treatment may be modulated to effect various survival fractions, and selective treatment of cell populations.

While strains which are desired to be treated may be found which are resistant to the system and method according to the present invention, supplemental methods may also be employed to treat the same medium, such as pulsed electric fields, oscillating magnetic fields, electron ionizing radiation, intense light pulses, actinic light or other visible or ionizing electromagnetic radiation, and high pressure treatments. Thus, treatments may be combined to effect complete Pasteurization or sterilization or more selective cell changes. See, Zhang et al., supra, Mertens et al., "Developments in Nonthermal Processes for Food-Preservation", Food Technology, 46(5):124–33 (1992), incorporated herein by reference.

The parameters of a bulk medium steam treatment process which control the efficiency include starting and ending temperatures, rate of temperature rise, degassing procedure (if any), pressure, pre- or post-treatments, pH, droplet size and distribution, droplet velocity, and equipment configuration. Presently, systems operable for milk Pasteurization have been tested using various parameters. For example a test has been conducted with a temperature rise from about 46° C. to about 70.8° C., with a milk pH of 6.60 (start) to 6.65 (finish), and a dilution of 2.5%. Droplet size is preferably about 0.2–0.3 mm. The rate of temperature rise is, for example, in excess of 1500° C. per second, and more preferably above 2000° C. per second. Under these conditions, with a starting bacterial and spore concentration of 10,000 spores per ml, the final concentration was 12 per ml. Thus, a reduction of about three logs was achieved under these conditions, without, for example, sedimentation of milk protein or noticeable alteration in taste.

The bulk medium steam treatment apparatus according to the present invention provides a rapid temperature rise by subjecting relatively small droplets of less than about 0.3 mm to dry steam (non-supercritical) at a partial pressure less than about 760 mm Hg. For example, with a low partial pressure of non-condensing gasses (e.g., less than about 100 mm Hg, and more preferably below about 50 mm Hg), the partial pressure of steam is about 0.3–0.8 atmospheres (e.g., about 225–620 mm Hg). The steam is saturated, and thus the temperature of the steam is held at a desired final temperature, e.g., 40–75° C. The steam temperature-pressure relationships are well known, and need not be reviewed herein.

Droplets of medium including cells to be treated are atomized under force through a nozzle, into a reduced pressure reactor chamber containing the steam. Under this partial vacuum, residual gasses are drawn out of the droplet, which may form a boundary layer, reducing heat transfer rate; therefore, it is preferred that the bulk medium to be treated is degassed prior to treatment. Along its path, the droplets contact steam, which condenses on the relatively cooler droplets and heats the droplets through release of the latent heat of vaporization. As the steam condenses, the droplets are heated, until they reach the equilibrium temperature of the steam, at which time there is no further net condensation of steam. The droplets will not get hotter than the steam in the chamber, so that the steam temperature sets the maximum temperature. However, depending on reactor configuration, the droplets may not reach equilibrium, and thus may reach a maximum temperature somewhat cooler then the steam. Of course, the initial interaction of the droplet with the steam will produce the highest temperature change rate, so that the reactor system may be designed to operate at a steady state which does not achieve equilibrium temperature. In this case, however, parameters should be tightly controlled to assure complete treatment without overtreatment, and thus a maximum temperature above a desired level.

The condensation of steam on the droplets induces pressure variations, or more properly steam partial pressure variations, within the reactor. In order to prevent a buildup of non-condensing gasses through outgassing or impurities, a vacuum pump may be provided which continuously withdraws gas, with a port near the droplet injection nozzle, removing the non-condensing gasses and some steam. Preferably, however, the product to be treated is fully degassed prior to entry into the reactor, and thus there will be little or no buildup of non-condensing gasses which require evacuation from the reaction vessel during processing. The droplet rapidly equilibrates with the steam temperature under the pressure conditions, over a distance of less than one meter, for example within 70 mm from the droplet injection nozzle. The so-treated droplets are then collected, and may be immediately cooled, thus limiting any adverse effects of long-term exposure to the steam temperature.

In one embodiment, the reaction vessel is provided with a number of zones which maintain steady state distinction. For example, in an initial portion, a low absolute pressure is maintained, degassing the droplets. In a subsequent portion, the droplets are contacted with steam, resulting in a rapid temperature rise of the droplets to effect the desired treatment. In a final section, a low steam partial pressure is maintained, allowing vaporization of water from the droplets, allowing flash cooling. In this manner, the time temperature product may be held at very low levels, effecting a rapid temperature increase followed by a relatively rapid temperature decrease. In order to provide separate temperature zones within the reactor, an external energy source within the reactor may be provided, such as infrared radiation source, to maintain steam temperature. Zones may also be separated by baffles which allow droplets to pass, while providing a gas flow restriction.

The steam in the preferred embodiment is provided by a steam generator, which boils, for example, potable or distilled water. This water is degassed prior to use, so that the steam contains few impurities and almost no noncondensing impurities. The steam generator may be at any temperature above the final temperature, e.g., 150° C., as the thermal treatment of the droplets derives mainly from the latent heat of vaporization of the droplets, and very little from the absolute temperature of the steam. Preferably, the steam is saturated, which will define its temperature in a given atmosphere. If the steam is sub-saturation, condensation of steam on the droplets will be impeded. If the steam is supersaturated, it will itself form droplets and impede the process, in addition to diluting the medium. Process temperature control will also be adversely affected, and may be less predictable.

Thus, the mass flow rate of the saturated steam entering into the treatment system (in relation to the product flow rate and any withdrawal of steam or external heat transfer), controls the process treatment temperature. In the case of an over-pressure steam generator, the mass flow rate is restricted to prevent the treated droplets from reaching too high a temperature, or supersaturation conditions.

The steam is injected adjacent to the path of the droplets being treated, to ensure equilibration by the time the droplet reaches the terminus of the reactor. Due to boundary layer effects of the droplet, due to, for example, non-condensing gasses, as well as diffusion limitations, the temperature rise is not instantaneous. However, using the system in accordance with the present invention, it has been found that temperature rise rates in excess of 2000° C. per second, or even 7600° C. per second, may be achieved, which are sufficient to inactivate bacteria, and thus will effect may different types of cells and cellular structures.

It is therefore an object of the present invention to provide a new treatment modality for disease, that of high temperature rate changes without necessity of thermal denaturation.

It is a further object according to the present invention to provide a method and system in which a rapid heat treatment is applied to the bulk of a product, with a temperature rise of several thousand degrees per second. Preferably, the time and temperature conditions are insufficient to denature proteins, although this is not an absolute limitation.

It is a still further object according to the present invention to heat a product at a rate sufficient to cause a thermal shock effect on cells contained therein, reaching a final temperature for a period which preferably does not cause substantial thermal denaturation.

High temperature change rates are needed in order to overcome the relaxation rate of structural changes in a membrane structure, e.g., the cell membrane. A bacterial membrane, for example, relaxes over a period of about 10–100 ms. Thus, where the temperature rise rate exceeds the relaxation rate, the membrane appears non-compliant, and is therefore especially subject to stresses which cause irreversible damage or at least produce a non-transient effect. Therefore, the absolute temperature rise as a result of the rapid heating should produce sufficient stress to effect the cell in a non-transient manner. In this sense, non-transient means that an effect lingers after the treatment is completed and does not merely represent a reversible temperature induced physical effect.

Therefore, for example, the temperature rise should be at least about 1–2° C. for a mild effect, and possibly 15–100° C. to assure cell death or inactivation. Of course, the absolute temperature rise may depend on temperature rise rate, as well as other reaction conditions. Generally, for cells of medical interest, the absolute temperature rise will be less than about 40° C., with a maximum temperature of less than 50° C.

The present bulk medium steam treatment apparatus according to the present invention therefore differs qualitatively from the known thermal denaturation (Pasteurization) processes and known medical processes. The quality of the product and efficacy of the process are not in direct relationship to each other, allowing an improvement in the efficacy without detrimental effects.

Studies have shown that viable bacteria may be reduced or eliminated in foodstuffs, even to the limits of detectability, by a high rate of temperature increase,. and therefore such processes may be employed where such bacterial reduction is desirable or required.

The preferred rate of temperature change for bacterial reduction is in excess of about 2000° F. per second, and should be greater than about 1100° C. per second. This rate of change is difficult to achieve through a direct contact process, where a mass of product to be treated is high, or the available surface area is low, due to the limits on thermal diffusion through the surface layer and thermal inertia. However, the by passing small liquid droplets through a controlled steam chamber, the desired temperature rate of change may be obtained.

In the bulk medium steam treatment device, the medium is sprayed through a nozzle as a stream of small droplets into a reaction vessel. The size of these droplets is preferably less than 0.3 mm, though if the droplets are too small they may present other difficulties, such as poor trajectory control, e.g., from low inertia, loss of velocity, e.g., due to drag, Brownian motion, coalescence, and the like. Further, reduced droplet size may reduce potential throughput. In addition, since, if the droplet is too large, each drop of the medium may not be effectively treated, the droplet size distribution should include only a small umber of larger droplets, e.g. less than 1% of greater than 0.45 mm. Steam, which is produced in a steam generator, from, e.g., potable water, is supplied to the reactor vessel through a nozzle or array of nozzles. Steam condenses on the droplets, giving up its latent heat of vaporization to the droplets. The magnitude of heat transfer during condensation is very high, so that the speed of heating reaches several thousand degrees Centigrade per second. Therefore, in the several milliseconds it takes for droplets to travel through a reaction vessel, the temperature is raised substantially, effecting cellular alteration, e.g., bacterial inactivation, according to the present invention.

The steam is derived from a boiler. Tight control of temperature may require a high temperature boiler with a control valve near the reactor vessel. In other words, in order to ensure adequate flow of steam into the reactor, an excess capacity should be available from the boiler. Control is effected near the reactor, to avoid time response delays or oscillation. The water in the boiler is preferably degassed to eliminate non-condensable components.

The steam is injected into the reactor vessel through a number of steam injection ports, spaced along the path of the droplets within the chamber, so that the region distant from the fluid injection port maintains a relatively constant water vapor pressure. Thus, depending on the desired conditions, effective Pasteurization may be obtained with as low as between 2–5% by weight steam, condensed on the fluid droplets to achieve the temperature rise. There are temperature gradients in the reactor chamber, primarily near the injection nozzle. Since the steam condenses on the droplets, a partial vacuum is created in the region around the droplet, until the droplet reaches a temperature in equilibrium with the pressure, e.g., around 55° C. at 0.5 atmospheres, and thus the vapor pressure equalizes. At equilibrium, the net condensation ceases, and the droplet remains in equilibrium.

The steam consumption is significantly lesser than in known ultra high temperature Pasteurization processes. Assuming the temperature of heat treatment applied to milk is to 60° C., the temperature of milk upon entering the reaction vessel equal to 6–8° C., then the required temperature rise will not exceed 55° C. It will require about 55 Kcal for the heat treatment of one kilogram of fluid medium. As the condensation heat of one kilogram of steam is equal to 540 Kcal (540 cal/ml), only about 0.1 kilogram of steam will be required for condensation, i.e., only 10% of the mass of the product subjected to processing. Obviously, lesser temperature rises will require less steam.

It is noted that there is no need to subject the product, for instance, milk, to heat treatment reaching a maximum temperature of 60° C.; however, higher temperatures may be reached if desired. Since it is temperature rise rate which is believed to be important, lower maximum temperatures may be achieved. For example, bacterial inactivation has been achieved even at a maximum process temperature of about 40° C., thus making the requirement for steam consumption generally less than 7% of the mass of the medium undergoing Pasteurization.

The treated fluid medium, which has been slightly diluted with condensate, is collected on the bottom surface of the reaction vessel and then is supplied through a special vent into the discharging tank. The collected medium is subjected to a vacuum treatment, evacuating gases (air) and steam from the discharge, thus eliminating excessive water, cooling the fluid medium through water evaporation, as possibly through an external cooling system. The fluid medium may then, for example, constitute a final product or be used as part of a medical treatment.

The thermal shock treatment system has been tested for effective Pasteurization of milk and other fluids, in apparatus having a productivity of up to 1000 kg/hour. The following substances were subjected to Pasteurization: physiological solution, milk, egg melange, blood plasma. All of these fluent materials, prior to subjecting to Pasteurization process, were disseminated with $E.$ $coli$ in a concentration equal to $10^7$ per ml. After treatment, the concentration of $E.$ $Coli$ either reached the lower limit of sensitivity of the method of their detection (0.0001%) or they were not detected at all, thus attesting to full sterilization process. There was no evidence of fluid protein thermal denaturation. The $E.$ $Coli$ culture and the experimental studies of the Pasteurized products was prepared by the staff of the Microbiological laboratory of the Medical Radiological Research Center of the Medical Academy of Russia, using standard methods.

The experimental studies carried out have determined that, in order to produce "Pasteurized" milk with a bacterial concentration not exceeding 50,000 bacteria per ml (which corresponds to the grade 1 quality milk), from starting milk product with a bacterial concentration of 1–10 million per ml, the heat treatment rate should be equal to or greater than about 1400° C. per second, and for producing sterilized milk, it should be equal to or greater than 7600° C. per second. The maximum temperature of sterilization does not generally require a temperature in excess of 60° C., while retaining all the positive qualities of natural milk. Higher maximum temperatures may be employed.

One of the significant results reveals itself in the fact that due to low temperature and short term heat treatment, it is also possible to treat such fluent products as egg white, even though such material is subject to coagulation upon reaching the temperature of 52° C.

Positive results have been achieved during blood plasma treatment. The present invention can thus be utilized for Pasteurizing fruit and vegetable juices, wines, beer, yogurt produce, drinking water, pharmacological substances, etc.

The present invention provides efficacious treatment allowing full sterilization of a fluid without substantially detrimentally thermally denaturing proteins. It allows production of high quality dairy products including baby food, the production of which has previously been under constraints because of low quality Pasteurization. This is achieved through utilizing a new technique of incapacitating microorganisms and a different modality of destruction; high speed, short duration thermal treatment.

The present invention:
1. requires heat treatment within a small temperature range, and therefore is less power consuming.
2. allows the fabrication of treatment equipment free of heat transfer apparatus, thus eliminating sediments on relatively hotter components, and thus eliminating necessity of its cleaning involving the usage of chemical agents (acids and alkali).
3. allows the fabrication of both large-scale treatment equipment for plant installations with productivity of tens of tons per hour, as well as smallscale treatment equipment or even reactors having a throughput of milliliters or liters per minute. Such smaller scale equipment may be useful for small business, home or medical usage.
4. allows manufacture of reactors utilizing different sources of heat treatment (steam in plant environment, electrical heating and organic fuel in small scale environments).

In a typical bactericidal treatment system, a temperature rise of a liquid to be treated is from about 25° C. to about 55° C. For example, in a reactor 30 cm high, with a droplet velocity of 20 m/sec, the residence time will be about 15 mS. Thus, assuming an inlet temperature of 25° C. and an outlet temperature of 55° C., the temperature change is 30° C. over 15 mS, or about 2000° C. per second. Typically, the temperature rise will not be linear, nor will equilibration require the entire reactor length, so that the maximum temperature rise rate will be well in excess of 2000° C. per second.

The liquid to be treated may be degassed prior to processing, to prevent accumulation of non-condensing gasses within the steam treatment reactor and resultant alteration of the thermodynamic operating point. Further, by degassing the liquid prior to interaction with the steam, the interaction with, and condensation of, steam on the fluid droplets is facilitated. Preferably, non-condensing gasses are kept to less than about 50 mm Hg, and more preferably less than about 20 mm Hg.

Alternately or additionally to degassing prior to dropletization, the fluid may be degassed within a first region of the reactor, under relatively high vacuum, after atomization, with subsequently reaction with the steam in a second portion of the reactor. Thus, due to the gas withdrawal in the upper portion, and condensation of the steam onto the relatively cooler droplet stream, steam will tend to flow from the second portion to the first portion of the reactor. Preferably, a baffle is provided between the two regions, with a relatively high density of fluid droplets to be treated, present in the transition region between the two portions, so that the steam condenses on the fluid droplets in this region, maintaining the pressure differential while effectively treating the droplets. Thus, steam vapor diffuses toward the fluid injection port.

In general, since the treatment chamber vessel operates at below 100° C., the pressure within the reactor will be below atmospheric pressure. For example, with an operating temperature of 55° C., the chamber will be held at approximately 0.5 atmospheres, or 380 mm Hg. Thus, the pressure in the chamber determines the operating temperature: if the pressure is too high, the necessary temperature to achieve that vapor pressure of steam increases or steam condenses, raising the temperature of the reactor, and vice versa. This condition is considered "wet". The control over processing is thus primarily exerted by the net mass flow of steam into the reactor. As stated above, a vacuum pump may be provided which exhausts non-condensing gasses and may also withdraw excess steam, allowing an additional control parameter and further allowing a non-equilibrium steady state to exist.

The walls of the reactor vessel should be maintained at least at or slightly above the final operating temperature, to avoid condensation of steam on the wall and unnecessary product dilution. This may be done by any suitable heating system.

In fact, a number of methods are available to prevent droplets which are insufficiently treated due to, for example, coalescence into large droplets or statistical variations droplet size during atomization, from contaminating the treated product. For example, the droplets may be electrostatically charged, and then normally diverted from a direct path. Droplets of too large a mass will be diverted less, and may be separately collected. Alternately, an entire stream segment may be diverted if a flaw (untreated or untreatable portion) in the treatment is detected. For example, an optical detector may detect a large droplet traversing the reactor and divert the outlet for a period of time to flush any contaminants.

It is believed that, as long as sufficient steam is present, small droplets will be effectively treated, while the persistence of bacterial contamination through treatment is believed to be related to the existence of large droplets. Thus, by eliminating or preventing large or untreated droplets, the effectiveness of the treatment is maintained.

The reactor may also include a second form of antibacterial treatment, such as ultraviolet radiation, which may be supplied by ultraviolet lamps illuminating within the reactor. Since the droplets are small, the light penetration will be high, thus ensuring full coverage. Likewise, microwaves or other radiation may me used for auxiliary heating of droplets to the desired temperature, or for an electromagnetic field treatment of the droplets.

Where a particular strain of bacteria is problematic, remediation efforts may be directed specifically toward that strain. For example, complementary bactericidal systems may be employed to reduce undesired strains.

Where the fluid to be treated contains other volatile compounds, such as ethanol, such vapors may evaporate from the droplets, especially at elevated temperatures. This produces two effects. First, a boundary layer is created by the net outward mass flow, which may impede steam contact and heating. Second, depending on the temperature and pressure, the droplet may be effectively cooled by the net loss of this other liquid component due to evaporation or boiling. Therefore, care must be taken to ensure that the fluid droplets do not reach the end of the reactor and pool prior to being raised to the desired temperature, or that the temperature rise rate is insufficient. If it does undergo the desired temperature rise rate, then the bacterial disruption effect is accomplished. Otherwise, it may be necessary to inject alcohol vapor with the steam to maintain equilibrium conditions in the reactor. It is noted that the reactor may also be used to reduce or vary alcohol concentrations of the fluid being treated, by varying the treatment conditions. For example, alcohol vapors may be withdrawn and captured through a vacuum pump, along with non-condensing gasses and some steam. This allows the production of a "light" alcoholic beverage, while killing yeast or other organisms.

It is noted that the reactor may effectively be used to treat milk, physiological solutions, fruit juices, blood plasma, blood serum, fruit and vegetable juices, potable water, egg white, beer, wine, egg yolk, sewage sludge, and atomized cheese.

Further, the reactor may be used for pharmaceutical processing, bioengineering processes, genetic engineering processes, vaccines processing, enzymatic extractions and other treatment processes where thermal shock is beneficial. These processes need not necessarily involve disruption of bacterial membranes, and may be used for other purposes. Therefore, the reactor may be used to initiate chemical reactions, activate coating powder or catalysts in chemical processes.

The present invention provides the advantage in pharmaceutical and bioengineering applications that the conditions of bacterial inactivation do not denature proteins, and may leave substantial bacterial structures essentially intact. Thus, in order to capture the product of bioengineering processes, the present method may be used, for example as an alternative to ultrasonic disruption of cells. The advantage of the present process over ultrasonic treatments is that it is essentially instantaneous in operation, power efficient, and may leave cells or cell fragments intact. This, in turn, allows the capture of antigenic structures for vaccines or the efficient processing of fragile biomolecules.

The present process may also have utility in the processing of natural or semisynthetic antibiotics, peptides or complex molecules. The present system may be used, during gentle treatment, to stress the microorganism into higher production of the desired compound(s), and to harvest the compounds(s) by killing the organism and releasing the intracellular contents, without denaturing proteins.

It is also noted that various non-biological compositions may have glass transition temperatures in the 25–300° C. temperature range, and therefore the present apparatus may be useful for using steam to rapidly alter a crystalline state of, e.g., these polymers, copolymers, block copolymers or interpenetrating polymer networks. This rapid limited heating may be advantageous, for example, to rapidly initiate a chemical reaction while maintaining a mechanical configuration of a bead, for example, if the time constant for the chemical reaction is comparatively fast with respect to the thermal diffusion time constant. Further, in larger droplets, an external polymerized shell may be formed around an unpolymerized interior.

Other objects and advantages of the present invention will become apparent from a review of the drawings and detailed description.

BRIEF DESCRIPTION OF THE DRAWINGS

The preferred embodiments of the invention will be explained by reference to the drawings, in which:

FIG. 1 is a simplified diagram of a reactor according to the present invention;

FIG. 2 is a detailed diagram of a reactor according to the present invention;

FIG. 3 is a partially schematic diagram of a processing system according to the present invention;

FIG. 4 is a partially schematic diagram of a processing system, showing details of sensor systems for control, according to the present invention;

FIG. 5 is a semischematic diagram of a processing system according to the present invention employing continuous mode degassification;

FIG. 6 shows protein sediment mass (mg) dependence on temperature of stainless steel surface at milk temperature of 20° C. and 35° C.;

FIG. 7 shows protein sediment mass (mg) dependence on temperature of zirconium surface at milk temperature of 20° C. and 35° C.;

FIG. 8 shows protein sediment mass (mg) dependence on temperature of stainless steel and zirconium surfaces for degassed milk during 30 min. at 20 mm Hg, at a temperature of 20° C.;

FIG. 9 shows protein sediment mass dependence on time of milk degassification on a stainless steel surface at 70° C.;

FIGS. 16A and 16B show a partial cross section and top view, respectively, of a Pasteurization reactor according to the present invention;

DETAILED DESCRIPTION OF THE PREFERRED EMBODIMENTS

Figure 1:
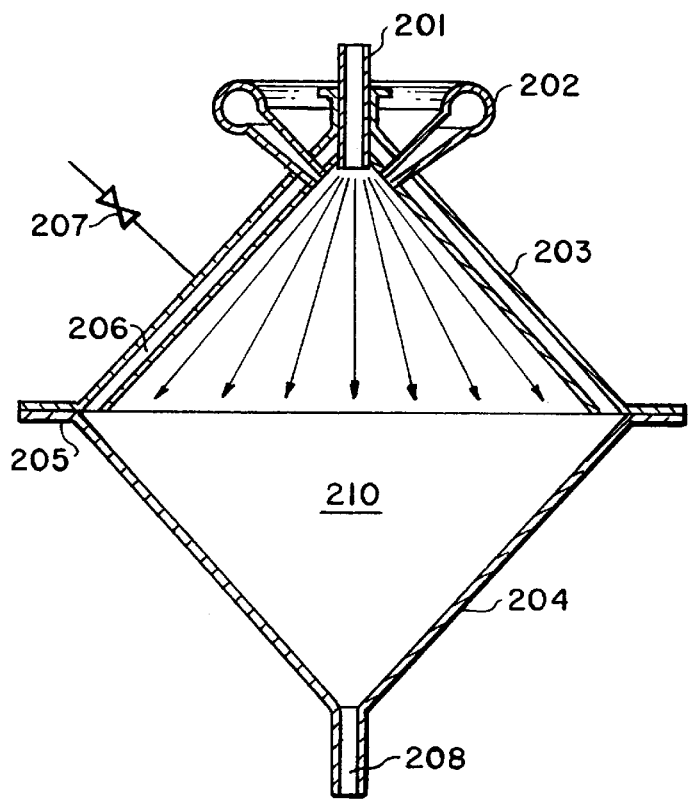
Figure 3:
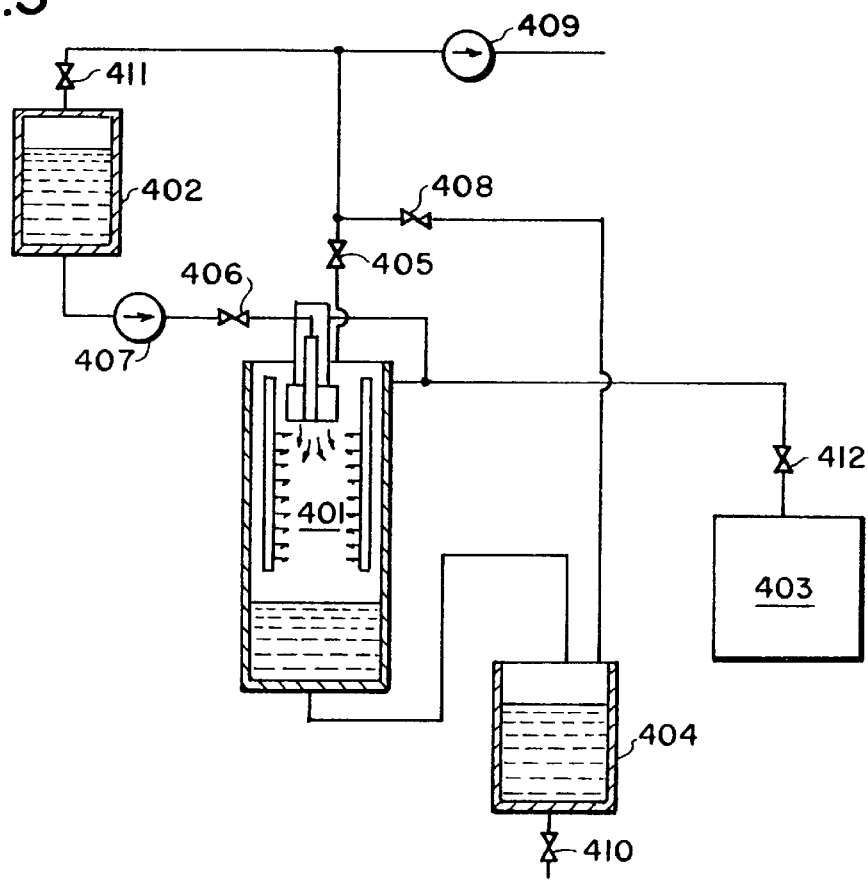
Figure 2:
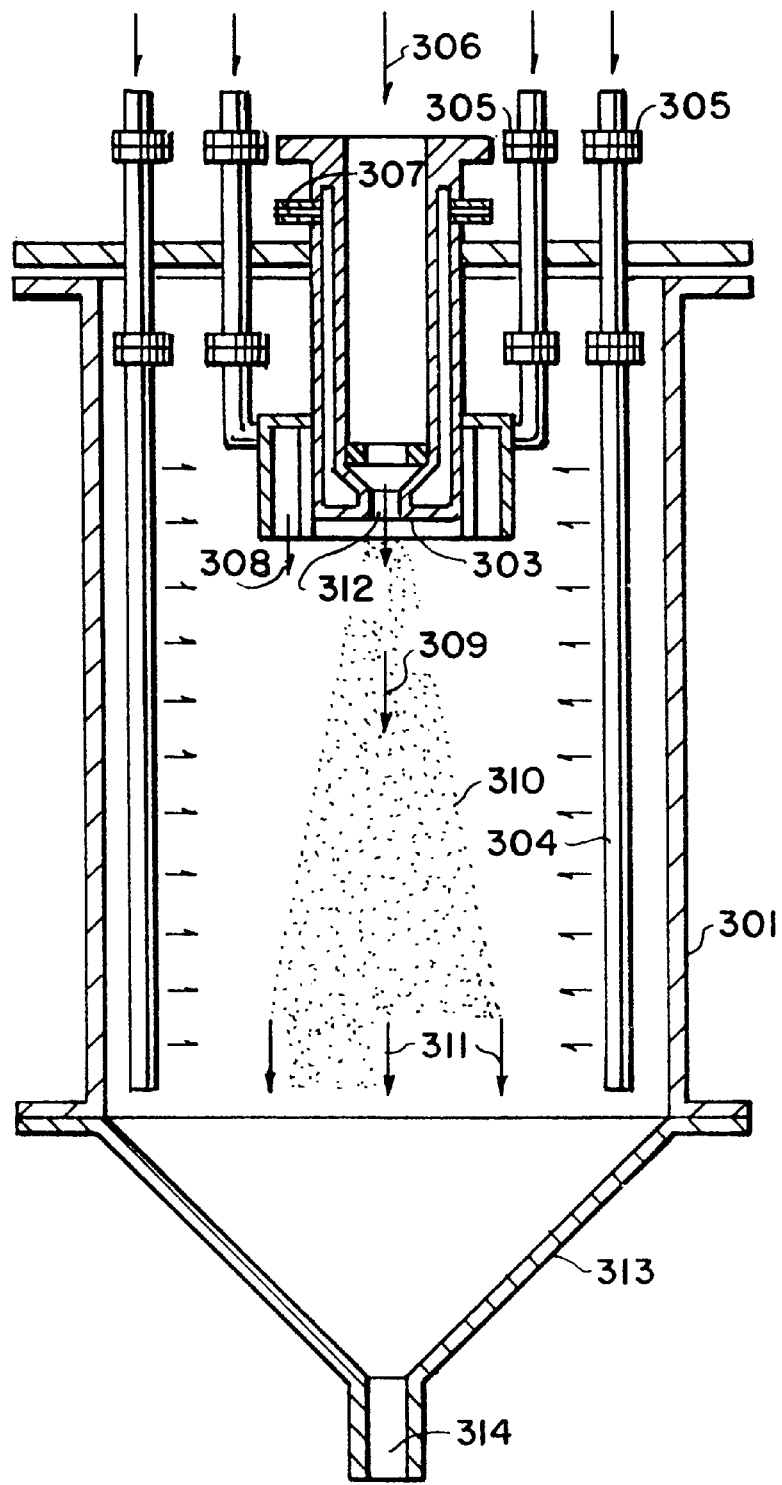

The preferred embodiments of the invention shall now be described with respect to the drawings, where identical reference numerals in the drawings indicate corresponding features.

EXAMPLE 1

FIG. 1 shows a simplified diagram of a steam condensation reactor vessel according to the present invention. The reactor is formed of an upper body 203 and a lower body 204, with a seal 205 therebetween. A fluid to be treated, which may be a growth medium, milk, or blood component, is degassed according to conventional procedures, preferably to a level of at most 50 mm Hg non-condensable gasses, and more preferably to a level of no more than 20 mm Hg non-condensable gasses. The degassed fluid enters the reactor at approximately 22° C. through a conduit 201 having an atomizer, which produces a spray of small fluid droplets, dispersed in the reactor space 210.

The pressure in the reactor is held at approximately 0.5 atmospheres by a vacuum control system 207, which is provided with a baffle 206 to prevent withdrawal of fluid to be processed. The baffle 206 also serves to insulate the reactor space from the upper body 203. The reactor space is filled with steam, e.g., substantially pure water vapor from steam injectors 202. The steam is provided at equilibrium, and thus the vapor pressure of the steam at the temperature of the reactor, i.e., approximately 55° C., is equal to the pressure of the reactor. Under such conditions, the steam will tend to condense on the fluid droplets, releasing their latent heat of vaporization, heating the droplets, until the droplets reach the temperature of the steam. As the steam condenses, a partial vacuum is created around the droplet, causing a net mass flow into the droplet. Depending on the exact reactor conditions, up to 10% by weight of steam may be absorbed, but generally the amount will be limited to 2–5%.

The droplets are ejected from the atomizer at approximately 20 meters per second. The total height of the reactor space is approximately 30 centimeters. Thus, the residence time of droplets within the reactor, before hitting the lower body 204, is at most about 15 mS. Therefore, the temperature of the droplets rises from 20° C. to 55° C. in about 15 mS, thus yielding a temperature rise rate of at least about 2300° C. per second. In fact, the maximum rise rate will likely be higher, because the steam equilibrates with the droplets before reaching the end of the reactor.

As the droplets hit the lower body 204, an accumulation and pooling takes place, and the fluid drains from the reactor space through exit port 208, assisted by gravity.

EXAMPLE 2

FIG. 2 shows a reactor in more detail. The reactor is similar in operation to the reactor detailed in Example 1. The reactor is formed of a cover 302, and a shell 301. A lower conical base 313 is provided below the shell 301. In this case, the fluid to be processed is injected through plenum 306, with an atomizer structure 312, which produces, e.g., 5 micron fluid droplets in a fast moving stream 309. Steam is injected through a dual manifold system 305, which includes series of central, upper injection ports 308, which provide a relatively high flow of steam near the atomizer structure 312, and a series of risers 304 which allow for reduced macroscopic pressure gradients within the reactor. In order to prevent undesired preheating of the fluid, a cooling jacket 307 is provided having circulating cooling water around the plenum 306.

The fast moving stream 309 reacts with the steam injected through the upper injection ports 308 and the risers 304, and becomes a heated fluid 310 at approximately the steam temperature. The heated droplets continue through the reactor, and reach equilibrium with the steam, as equilibrated droplets 311, and condense against the conical base 313 and exit the reactor through exit port 314. Preferably, a vacuum is drawn on the exit port to exhaust any accumulation of non-condensable gasses from the reactor during operation, to maintain the reactor in a steady state condition.

Table 1 shows various operating. parameters of a preferred reactor design according to the present invention.

TABLE 1

| Parameter | Milk | vapor |
|---|---|---|
| Flow Kg/hr | 1000 | 100 |
| Pressure in entrance of Processor | 0.4 | 0.1 |
| Steam temperature in Processor, ° C. | | 40–100 |
| Processor volume | 0.1 | 48.8 |

EXAMPLE 3

FIG. 3 shows a bactericidal system incorporating the reactor 401 described in Example 2. In this case, the fluid to be treated, e.g., milk, is provided in a degassification chamber 402, provided with a control valve 411 to a vacuum pump 409. The fluid is transported with a pump 407, through a valve 406, to the injection plenum of the reactor 401. The reactor 401 is also connected to the vacuum pump 409 through a separate valve 405 for startup cleansing of the reactor 401 and scavenging of non-condensable gasses. Pooled fluid accumulates at the bottom of the reactor 401, and is drawn to a processed fluid holding tank 404, where it may be drained through valve 410.

The fluid holding tank is also connected to the vacuum pump through valve 408, to allow a gradient for withdrawing processed fluid from the base of the reactor 401. A steam generator 403 provides steam through control valve 412 to the reactor 401, controlling the temperature in the reactor 401, e.g., between about 40° C. and 90° C., depending on the desired treatment conditions.

Tables 2, 3, 4 show experimental data for protein sediment mass based on various operating parameters of the reactor, as well as materials employed. It has been found that zirconium reactors produce significantly less protein sediment than stainless steel reactors under similar operating conditions. It has also been found that increased reactor temperature also results in increased protein sediment, for both zirconium and stainless steel. Finally, it has been found that degassification of the milk reduces protein sediment on the reactor, possibly due to reduced oxidation during the process.

TABLE 2

Experimental Data for Protein Sediment Mass Dependence on Surface Temperature

| Milk Temp 20° | | | | Milk Temp. 35° | | | |
|---|---|---|---|---|---|---|---|
| Stainless Steel | | Zirconium | | Stainless Steel | | Zirconium | |
| Temp ° C. | mg | Temp ° C. | mg | Temp ° C. | mg | Temp ° C. | mg |
| 48 | 0.45 | 36 | 0.45 | 54 | 0.6 | 55 | 0.85 |
| 50 | 0.65 | 45 | 0.65 | 62 | 1.25 | 64 | 1.45 |
| 62.5 | 2.2 | 56 | 1.2 | 70 | 1.85 | 71 | 2.55 |
| 65 | 3.6 | 63 | 3.8 | 79.5 | 3.85 | 78.5 | 3.45 |
| 64 | 2.5 | 64 | 2.5 | 90 | 4.6 | 87 | 4.4 |
| 76 | 4.85 | 74 | 4.9 | 96.5 | 5.35 | 96 | 4.7 |
| 78.5 | 7.25 | 85 | 7.0 | | | | |
| 81 | 9.2 | 94 | 8.25 | | | | |
| 89 | 9.45 | | | | | | |
| 93 | 9.35 | | | | | | |

TABLE 3

Experimental Data for Protein Sediment Mass Dependence on Surface Temperature

| Degassed Milk, 20° C. | | | |
|---|---|---|---|
| Stainless Steel | | Zirconium | |
| Temp ° C. | mg | Temp ° C. | mg |
| 37 | 0.83 | 46 | 0.65 |
| 52 | 0.85 | 52 | 0.6 |
| 62 | 0.95 | 62 | 0.65 |
| 74 | 0.88 | 73 | 0.75 |
| 90 | 0.92 | 89 | 0.80 |

TABLE 4

Experimental Data for Protein Sediment Mass Dependence on Oxygen Content

| In Milk for Stainless Steel Oxygen Saturated Milk | | Degassed Milk (20 mm Hg) | |
|---|---|---|---|
| Mixture time, min. | mg | Degassation time, min. | mg |
| 0 | 4.2 | 0 | 4.2 |
| 5 | 4.6 | 5 | 1.95 |
| 10 | 4.8 | 10 | 1.4 |
| 15 | 4.8 | 15 | 1.35 |
| 20 | 5.2 | 20 | 0.85 |
| 25 | 4.9 | 25 | 0.85 |
| 30 | 5.1 | 30 | 0.6 |

Figure 6:
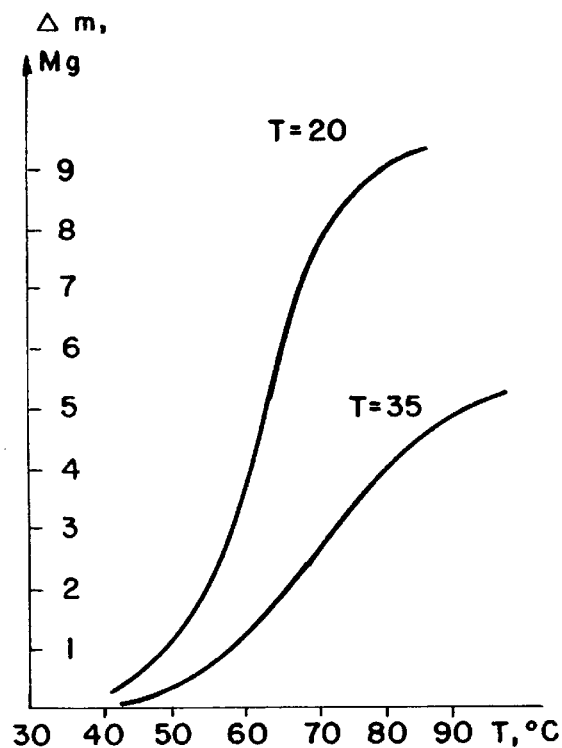

FIG. 6 shows protein sediment mass (mg) dependence on temperature of stainless steel surface at milk temperature of 20° C. and 35° C.

Figure 7:
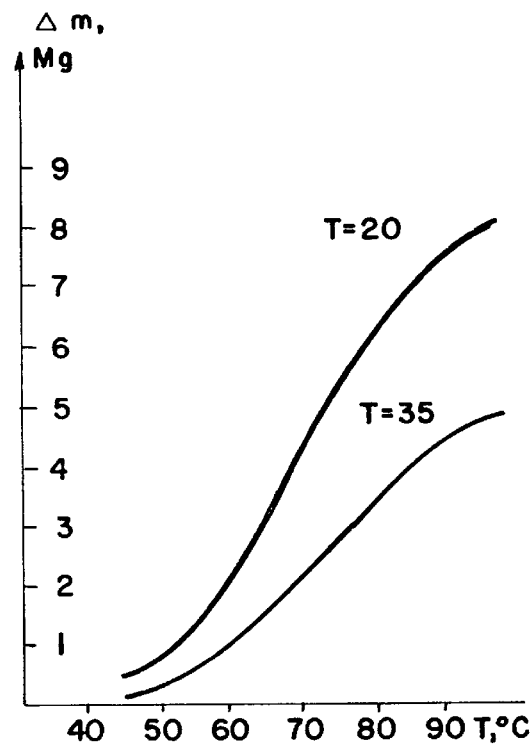

FIG. 7 shows protein sediment mass (mg) dependence on temperature of zirconium surface at milk temperature of 20° C. and 35° C.

Figure 8:
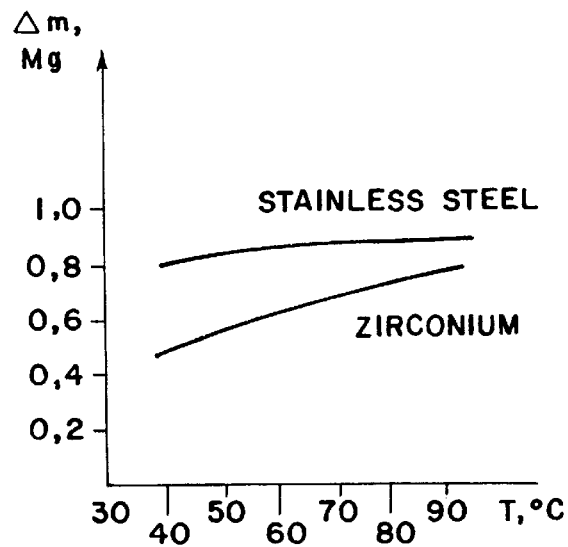

FIG. 8 shows protein sediment mass (mg) dependence on the temperature stainless steel and zirconium surfaces for degassed milk during 30 min. at mm Hg, at a temperature of 20° C.

Figure 9:
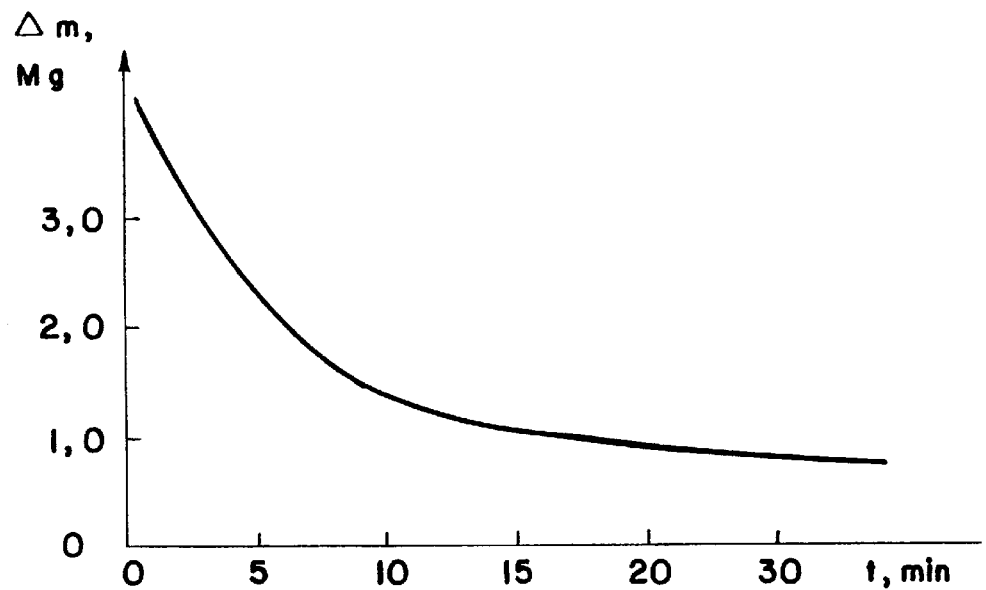

FIG. 9 shows protein sediment mass dependence on time of milk degassification on a stainless steel surface at 70° C.

Figure 10:
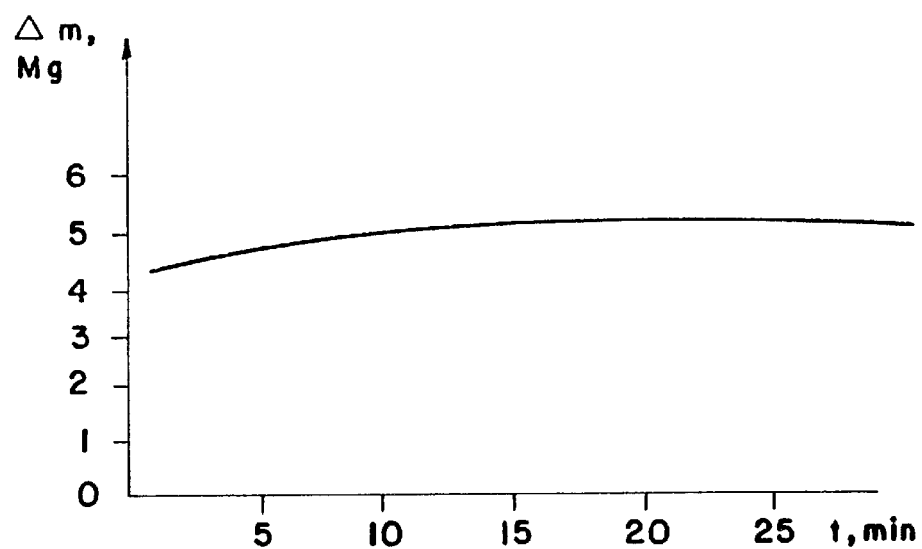
FIG. 10 shows protein sediment mass dependence on time of milk stirring (control) on stainless steel surface at 70° C.

FIG. 10 shows protein sediment mass dependence on time of milk stirring, without degassification, on stainless steel surface at 70° C., and thus serves as a control for the data of FIG. 9.

Figure 11:
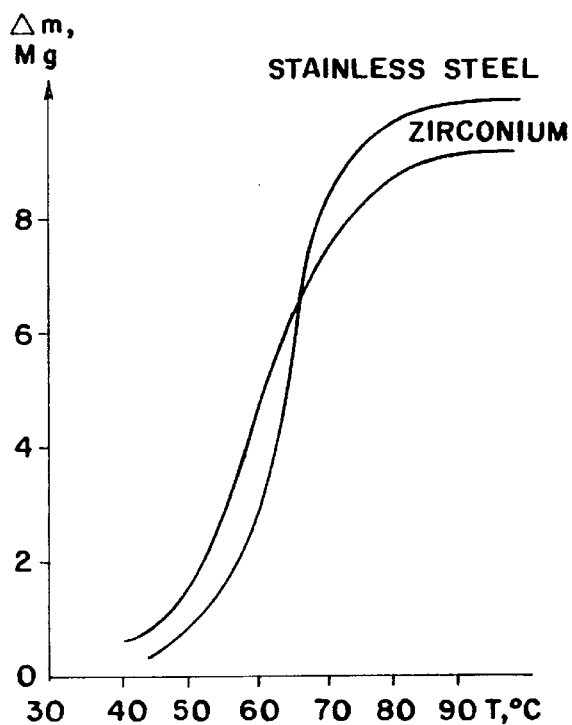
FIG. 11 shows protein sediment mass dependence on surface temperature for mixed milk on stainless steel and zirconium surfaces.

FIG. 11 shows protein sediment mass dependence on surface temperature for mixed milk on stainless steel and zirconium surfaces.

EXAMPLE 4

Figure 4:
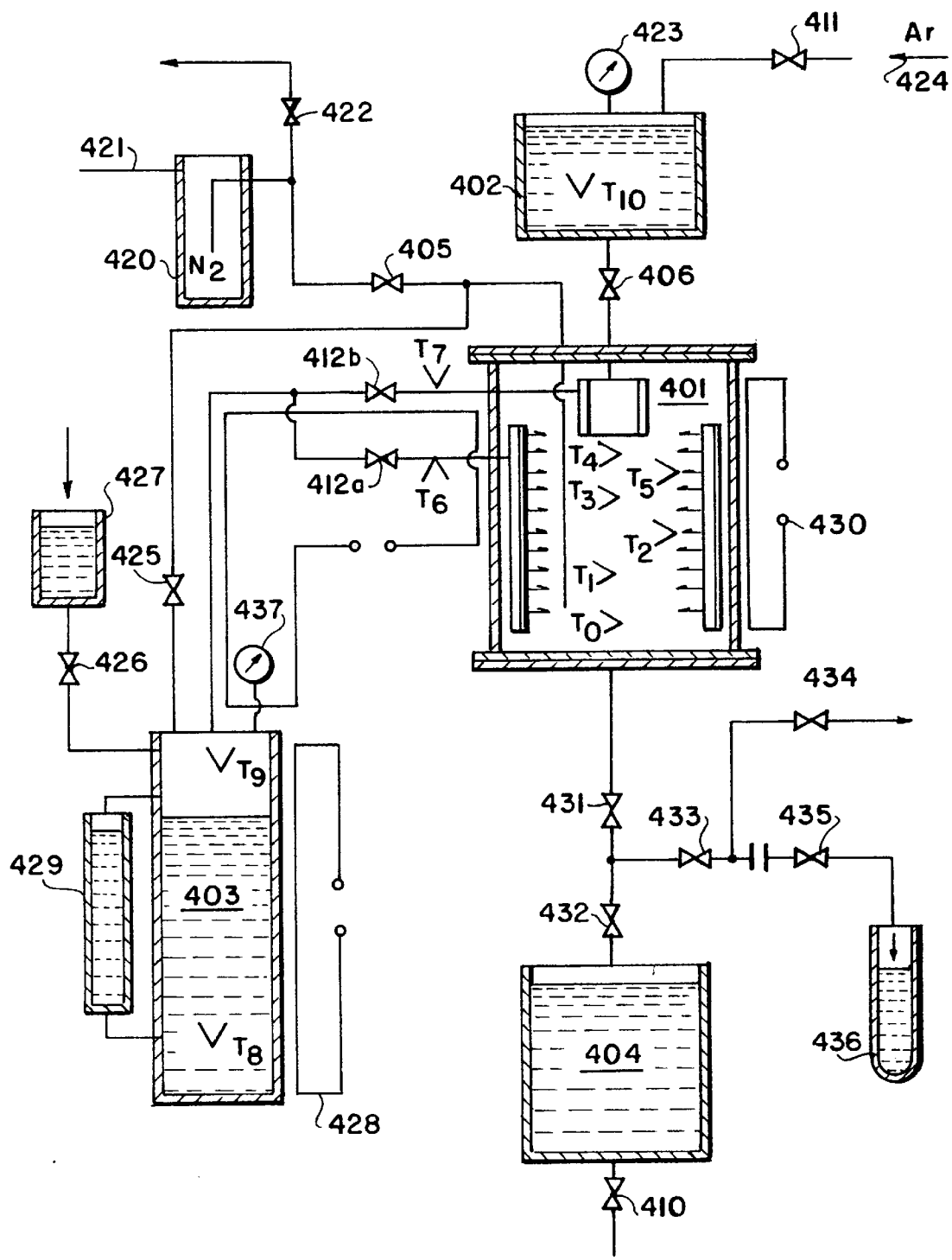

FIG. 4 shows a bactericidal system similar to the system described in Example 3, with the identification of elements for testing and controlling various conditions within the reactor system. In this system, the steam generator 403 is provided with a sight glass 428 for determining water volume, thermocouples T8 and T9 for determining temperature, pressure gage 437 and an electrical heater 428. Water enters the steam generator 403 from reservoir 427 through valve 426.

The degassification chamber 402, in this instance, shows a system which partially replaces air, with argon 424, through control valve 411. Thus, according to this embodiment, the motive force for driving the medium from the chamber 402 through the nozzle is the argon 424 pressure. While argon 424 is a non-condensable gas, the amount which dissolves is relatively low during a treatment period. A thermocouple T10 and pressure gage 423 are also provided. A heater 430 is provided to heat the outer shell of the reactor 401.

The steam is injected through a pair of control valves 412a, for an annular manifold and 412b, for a riser manifold, into the reactor. A pair of thermocouples T6 and T7 are provided to measure the steam temperature.

Within the reactor, a set of thermocouples T0, T1, T2, T3, T4 and T5 allow determination of temperature gradients within the reactor at steady state conditions.

To maintain vacuum conditions within the reactor, the vacuum pump (not shown in FIG. 4) acts through valve 422 and line 421 through water trap 420 and valve 405. The vacuum also acts through valve 434 to draw pooled fluid from the reactor 401, through valve 431. Valves 432, 433 and 435 allow use of sample 436, without disrupting reactor operation.

Figure 12:
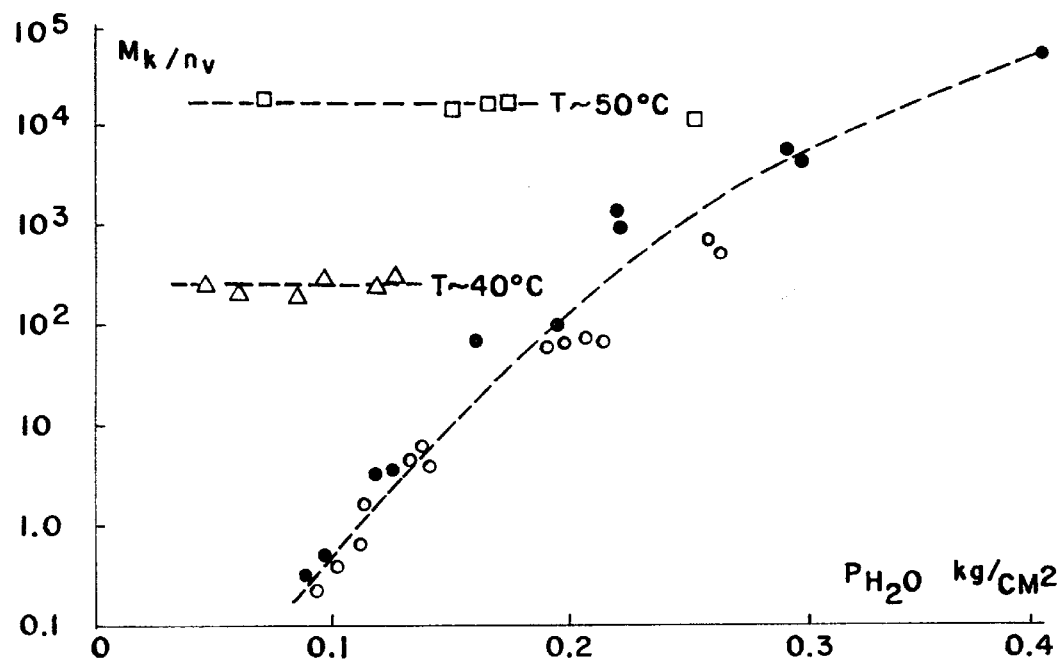
FIGS. 12 and 13 shows reduction of *E. coli* in milk in the reactor according to the present invention under various conditions.
Figure 13:
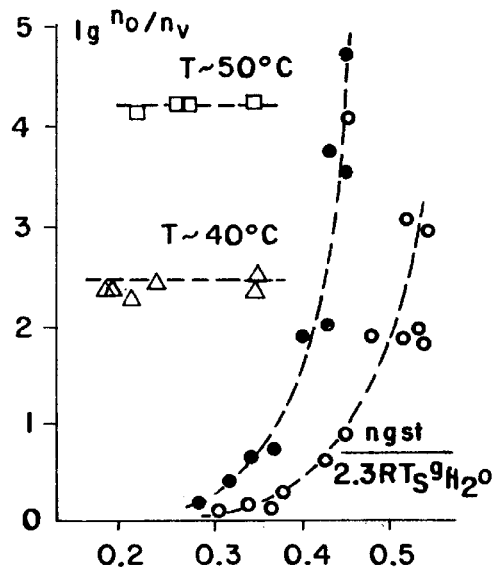

FIGS. 12 and 13 show results of testing the bactericidal effect of the reactor system according to the present invention. In these figures:

no is the initial concentration of *E. coli* (FIG. 13)

nv is the concentration of bacterial which survive treatment nk is the concentration of killed bacteria $P_{H2O}$ is the pressure of steam in reactor h is the heat of vaporization of water Ts is the saturation temperature of steam in the reactor R is the gas constant (8.31 g/kg K)

gst is the steam flow $g_{H2O}$ is the flow of processed liquid

○ without degassification of chamber

● with degassification of chamber

□, ∆ with degassification of the liquid

FIGS. 12 and 13 thus show that bacterial kill to survive ratios increase with increasing steam pressure (FIG. 12) and that degassification of the chamber improves bacterial killing as well (FIG. 13). FIG. 13 also demonstrates the effects of the relationship of fluid flow rate to steam flow rate.

Laboratory tests were conducted of various fluids containing E. coli, B. subtilis and mixed milk microflora. Tests were conducted of saline solution, milk, egg yolks, and blood plasma. 90% heating of liquid occurred within 1.5 to 20 mS. Table 5 shows results of E. coli in saline solution. The tests of other bacteria in other solutions produced similar results.

TABLE 5

| Sample No. | End Temp T, ° C. | Start Temp $T_0$, ° C. | surviving E. coli n, % | initial E. coli conc. $N_0$, $10^6$/ml |
|---|---|---|---|---|
| 1 | 50 | 13.2 | 1.4 | |
| 2 | 51 | 13.6 | 1.34 | 0.035 |
| 3 | 52 | 11.0 | 0.1 | 0.035 |
| 4 | 52 | 11.4 | 1.3 | 0.21 |
| 5 | 52 | 11.4 | 1.5 | |
| 6 | 52 | 11.4 | 0.078 | 0.035 |
| 7 | 53 | 23.2 | 1.3 | |
| 8 | 56 | 40.0 | 1.0 | 0.11 |
| 9 | 63 | 37.0 | 0.018 | 0.11 |
| 10 | 64 | 36.5 | 0.027 | 0.11 |
| 11 | 30 | 15.6 | 0.39 | 1.8 |
| 12 | 33 | 20.0 | 0.42 | 1.8 |
| 13 | 40 | 12.0 | 0.006 | |
| 14 | 41 | 24.7 | 0.46 | 1.7 |
| 15 | 42 | 23.8 | 0.37 | 1.8 |
| 16 | 42 | 17.5 | 0.43 | 1.7 |
| 17 | 44 | 19.8 | 0.32 | 1.7 |
| 18 | 50 | 32.8 | 0.007 | 0.22 |
| 19 | 50 | 31.0 | 0.096 | 0.22 |
| 20 | 52 | 30.6 | 0.006 | 0.22 |
| 21 | 59 | 12.0 | 0.009 | 0.21 |

EXAMPLE 5

Figure 5:
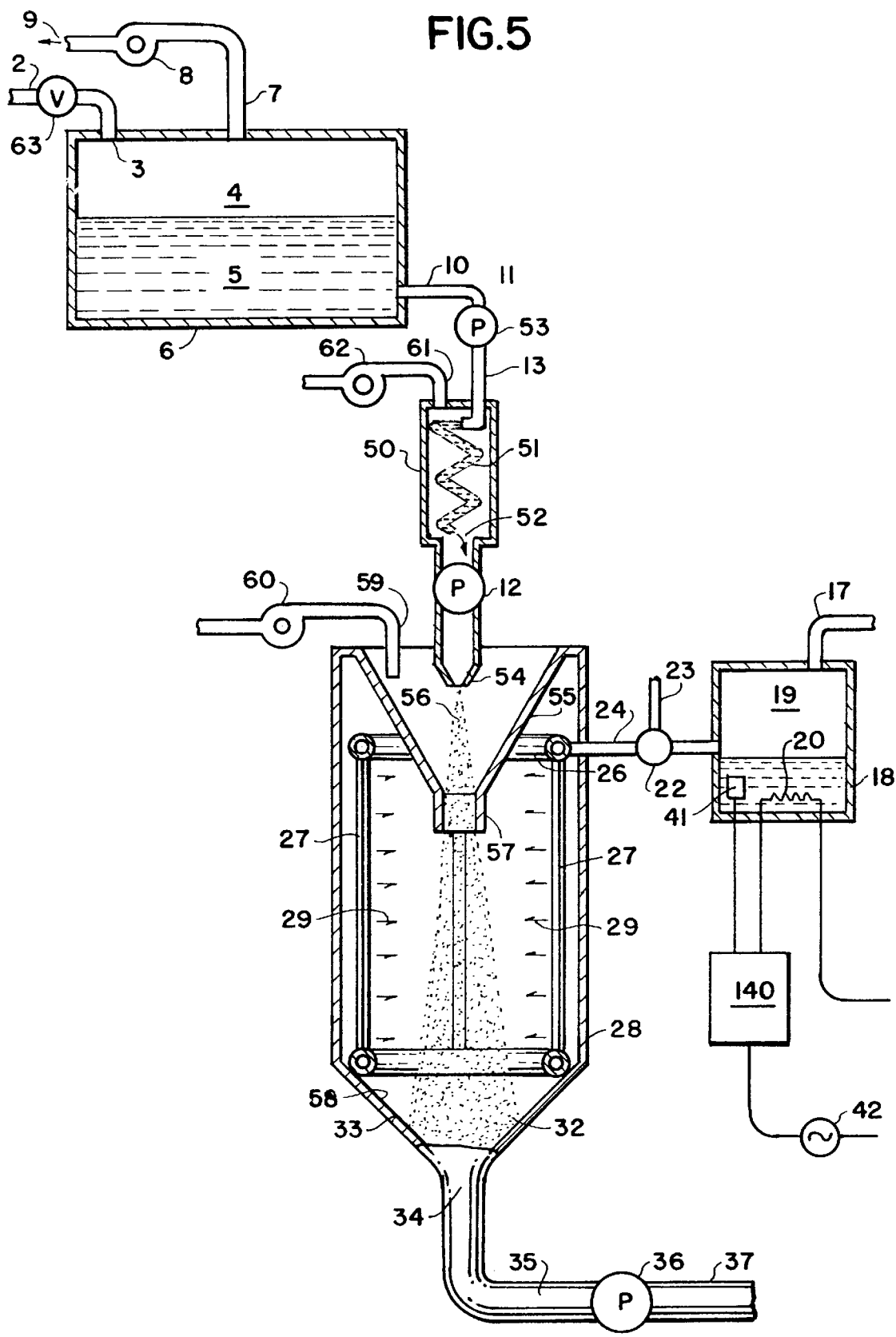

FIG. 5 shows a modified bactericidal system, as compared with Example 3, in which at least a portion of the degassification is performed in-line, rather than in primarily in batch mode. Further, the reactor forms a part of the degassification system.

A holding chamber 6 is provided for milk 5. A partially decompressed gas space 4 is provided, acted upon by a low vacuum pump 8 through vacuum line 7, to vent 9. This acts as a first stage of the degassification process. Fresh milk is fed to the holding chamber through an inlet conduit 2 having a valve 63 and inlet port 3.

The partially degassed milk 11 is fed through fluid feed line 10 to a feed pump 53, through line 13, to a vortex degassification system 50, having vacuum pump 62 through vacuum line 61. The milk 51 swirls under vacuum conditions to exit port 52, and is pumped into the processor with pump 12. The milk is then atomized within the reactor vessel, of the processor shell 28 and the conical pooling region 32, behind a baffle 55. The region proximate to the atomizer 54 is drawn under vacuum by vacuum pump 60 through line 59, to about 20 mm Hg pressure.

The atomized droplets 56 have a high surface area to volume ratio, and degas readily under these conditions. The degassed droplets pass through an aperture 57 of the baffle 55, and enter the main portion of the reactor vessel, coming into contact with steam at approximately 55° C. In this region, equilibrium is not achieved, and a net mass flow of steam will tend to be drawn upward through the aperture. However, since the droplets are cool, i.e., the milk stream is provided at approximately 22° C., and the droplets are further cooled by the degassification treatments, the steam will tend to immediately condense on the droplets, causing a rapid heating.

The steam 29 is injected into the reactor through a vertical steam distribution riser system 27, fed by steam distribution manifold 26, through steam injection line 24, pressure regulator 22, with relief port 23, from steam generator 18 having steam space 119. The steam generator is heated electrically by electrical heater 20, controlled by control 40 with temperature sensor 41 and power source 42. Water is fed to the steam generator 18 through water feed line 17.

Processed milk 58 contacts the conical neck 33 of the reactor and pools 34 at the lower portion, and is withdrawn through outlet line 35, through pump 36, to processed milk outlet 37.

EXAMPLE 6

A pilot plant reactor system is shown in FIGS. 14–17. This system allows optimization of process parameters, and is capable of continuous operation, however, as a pilot plant, is generally is operated with a 15 liter fluid reservoir. The system operates on the principle of heating droplets using condensing steam in a vacuum chamber, which is held a constant subatmospheric pressure by a vacuum pump. The pressure within the steam generator is measured with a compound pressure and vacuum gauge 612. The atomization of the fluid is implemented through a nozzle, into which the product is fed under the pressure, for example generated by and inert gas (argon) source, at a pressure in excess of 4–5 atmospheres, through gas/vacuum valve 613. The level of water within the steam generator may be determine by viewing the glass level gauge 611.

The major components of the system, exclusive of controls, include a steam generator 601, a Pasteurization reactor 602, a raw product tank 603, a Pasteurized product tank 604, a vacuum collector 616, a drain tank 606, a condensate tank 607, and an inert gas feed-in system to the raw product tank 609.

The vacuum system includes water circuit pump 626 and vacuum oil pump 620, which can operate individually or following the scheme: the gasses from the vacuum collector 616 are pumped out to a vacuum pump 620, and/or to a water circuit pump 626. In order to avoid water condensation, or to diminish same, in an oil vacuum pump 620, a steam condenser 621, which has its own water feed-in 622 and feed-out system, is installed between the reactor 602 which undergoes evacuation and the pumping system. The vacuum collector 616 drains to a condensate tank 615.

Product steam processing control feedback is implemented through a thermocouple (<1° C. resolution) and diaphragm pressure gauges (10 Pa resolution). Thermocouples are installed in the water and steam units of the steam generator 601, in the reactor 602 near the nozzle as shown in FIG. 17, located near the top of the reactor 602 (seven in all) for the purpose of gauging temperatures in a steam-droplet mixture at the product drain line 631 in the reactor 602, and in the tanks of raw 603 and Pasteurized 604 products.

Pressure is measured in a steam collector 632 and in the bottom part of the reactor 634. In addition, it is possible to sample the steam-droplet mixture from the vacuum lines of the reactor 635, 636 for its subsequent analysis on a mass-spectrometer 623 of the mass spectrometer system 639. The sample to the mass spectrometer 623 is passed through a mass spectrometer sampler tank 618, the pressure of which may be determined by pressure gauge 617. A vacuum pump 619 draws the sample gas into the mass spectrometer sampler tank 618. The mass spectrometer is connected to a magnetodischarge diode cooled pump 627.

Vacuum processing of the reactor 602 during operation is implemented in two locations: in the upper part 635 of the reactor 602, near the nozzle 637 for the purpose of degassing raw product from tank 603; and in the bottom part 636 through the reactor 602, around a system of shields, which is the main passage to the vacuum processing system.

Samples of the processed product are taken directly from the stream of the processed product, into disposable syringes, through the drain line 606 of the reactor 602.

The Pasteurizer reactor system consists of a number of components. A nozzle 637 (sprayer) for atomizing milk or any other liquid product to be Pasteurized, into drops. The nozzle 637 is of a standard, centrifugal, dismantling type. The outlet ring 646 of the nozzle 637 is replaceable, its diameter being equal to 4.8 mm for the water consumption of 1 liter per second at a pressure 0.4–0.5 MPa and 2 mm for the water consumption of 0.15 liters per second. The vortex segment 647 of the nozzle 637 has the following dimensions: diameter equal to 27 mm, with the height of the cylindrical part equal to 6.5 mm. The vortex forming ring 645 has 6 triangular grooves 3.2×3.2 mm at an angle of 45° to the horizontal plane. There is an inlet 648 in the center of the ring 645, the diameter of which is equal to 3.6 mm. When the inlet 648 is closed, the nozzle 637 is operating as centrifugal. When the inlet 648 is open, operates in a jet-centrifugal mode. The jet-centrifugal mode of the nozzle 637 fills the cone practically to capacity at a dispersion angle of 90°. The purely centrifugal mode of the nozzle 637 has the center of the cone empty, but the drops are of more homogeneous dimensions. The nozzle has a non-toxic rubber seal 643.

The body of the reactor, is attached to the shield 704 and the steam collector 705, with inlets of 5 mm in diameter for steam dispensing the reactor. The placement of the inlets and their number are optimized by way of empirical testing depending upon the product consumption and the dimensions of its drops. The upper part of the steam collector 705 includes two welded pipes 720 for dry (or slightly super-heated for 10° C.–20° C.) food steam. The non-condensing gas is evacuated through the space between the shield 704 and the outer body 721 of the Pasteurizer reactor 700. Connector 722 serves for evacuating the non-condensing gases from the bottom part of the Pasteurizer reactor 700 when there is no preliminary degassing of the raw product, and the degassing process is combined with deaeration. There is a circular groove 723 in the bottom part 706 of the body of the reactor 700 which serves for collecting and discharging of the condensate, which is forming during steam condensing on the body of the Pasteurizer reactor 700.

The bottom of the Pasteurizer reactor 706 is designed for collecting drops of the Pasteurized product, and its subsequent discharging into the tanks 604, 606, 607. The bottom 706 is sealed with a rubber rope gasket 724. There are tubes 725 designed for discharging condensate from the circular groove 723 located on the body of the Pasteurizer reactor 700 into the additional tank.

Food liquid to be treated in the Pasteurizer reactor 700 is broken up into small drops (diameter of approximately 0.2–0.3 mm) by the nozzle 637, on which steam condensing takes place. The drop heating speed and the efficacy of Pasteurization is better when non-condensing gases are eliminated by way of vacuum degassing.

The siphon 726 is attached to the lower part 706 of the reactor's 700 bottom, and has a welded seal for the thermocouple. The system features a siphon 726 to which a connection point 714 with a rubber ring seal 727, has been welded in the upper part of its body. This rubber ring seal 727 enables sampling of the product be taken immediately at the drain line of the Pasteurizer reactor 700 by piercing it with a disposable syringe.

Figure 14:
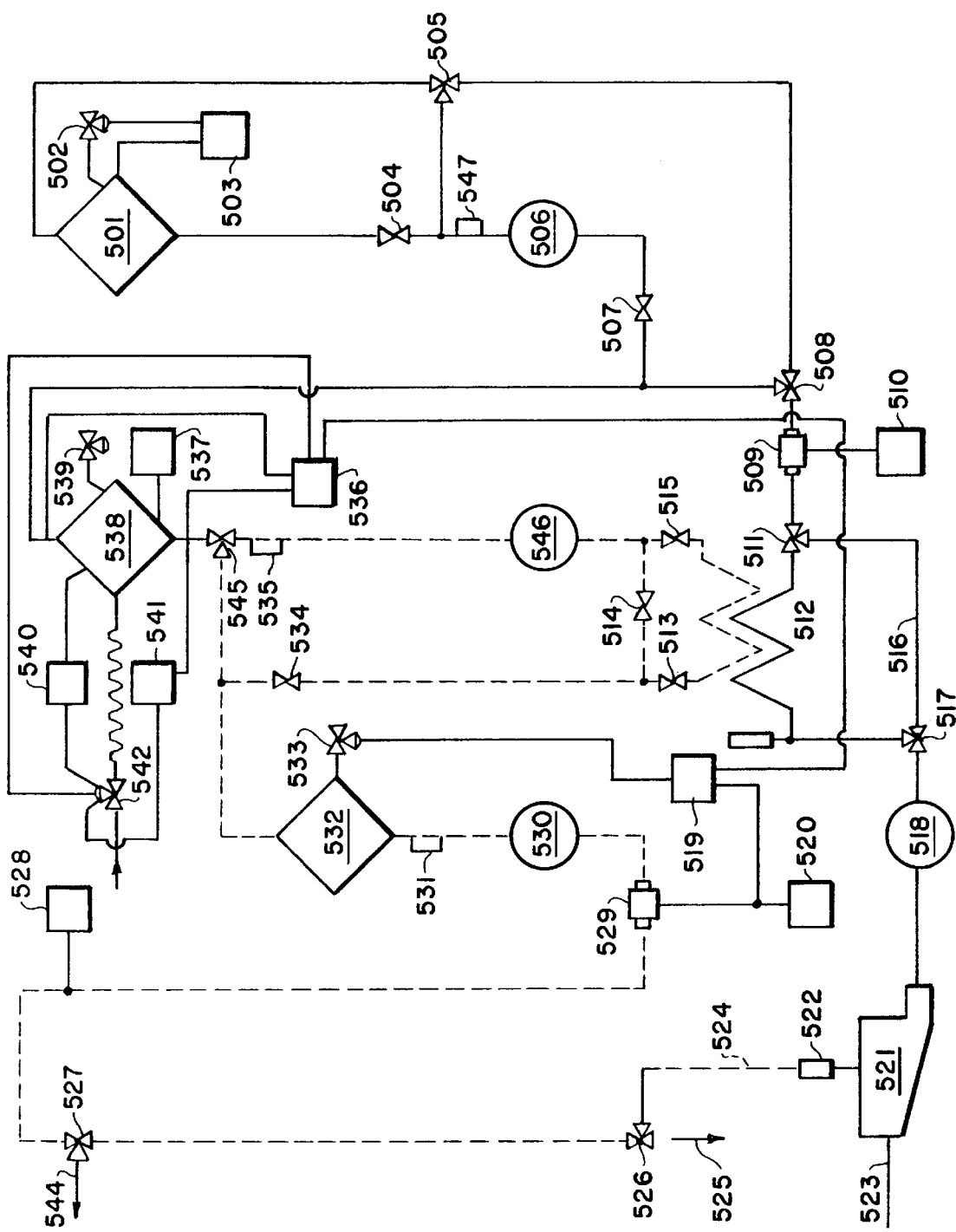
FIGS. 14 and 15 show schematic diagram of a Pasteurizer pilot plant according to the present invention as a flow diagram and process flow diagram, respectively.

As shown in FIG. 14, raw product 523 with a temperature, for example of 4° C. is fed into the tank 521 (constant level tank), and then is pumped by the pump 518 through valve 517 into the recuperator 512, where it is heated, for instance, up to 44° C. The heated product is then directed through valves 508 and 505 into the deaerator 501, where it is degassed, with a vacuum through the valve 502. At this time partial evaporation of the product is taking place and it is cooled down, for instance to 34° C. The deaerated product is discharged from 501 through product pump 506. Valve 504 and level sensor 547 provide the level, which is necessary for normal operation of the pump 506. Pump 506 feeds the product through Valve 507 into the Pasteurizer 538. All pumps 518, 506, 546, 530 can have similar parameters: capacity greater than or equal to 1 m³/hour, with a pressure no less than 0.4 MPa.

The Pasteurizer 538 reactor is pumped out, reaching the level of pressure approximately 10 Pa through valve 539, and is filled with dry, non-toxic, saturated steam reaching the level of pressure which correlates with the temperature of saturation, for instance, 68° C. Steam Pressure controller 540, with the help of an automatic steam valve 542, provides steam pressure at the inlet to the Pasteurizer 538 reactor which correlates with the specified temperature of saturation (68° C.).

The product is broken up to drops of specified dimensions, for example, 0.3 mm, and is heated up by steam condensation from 34° C. to, for example, 64° C. The heat-up speed is equal to up to 20–30 thousand degrees Centigrade per second.

Through valve 545 and the level sensor 535, the Pasteurized product is pumped out by the pump 546, and is directed into the recuperator 512 through valves 515, 513 and 514. The product is then cooled down in the recuperator 512 as low as, for instance 24° C. and is further discharged into the vacuum unit 532 through valve 534. Here the product is cooled down due to the evaporation into the vacuum, until it reaches the temperature of the raw product, e.g., 4° C.

The cooled down product is pumped out from the vacuum unit 532, through pump 530, and is fed through a magnetic flow meter 529 and Valve 527 either to the drain line 525, through which Pasteurized product is discharged, or into the recirculation line 524 through valve 526, and then into the constant level tank 521 through sight glass 522.

If the temperature of the cooled Pasteurized product is equal to the temperature of the raw product, then dilution of the product with food steam is approximately equal to zero. The precise balance between the water which is induced into the product and then removed from it, is sustained by the Ratio Controller 519, by balancing gas pressure in the vacuum chamber 532.

During optimization of the Pasteurization system, automatic steam valve 542 has to be monitored by the Steam Pressure Controller 540 at the input to the Pasteurizer 538 reactor, by temperature monitor at the output from Pasteurizer 538 reactor and the thermal shock controller 536. After this system is optimized, this valve will be controlled by one of the mentioned controlling mechanisms (most likely the thermal shock controller 536).

It is feasible to eliminate the preheating in the recuperator 512. In this case the product is fed through bypass 516 and further on into the deaerator 501 and into the Pasteurizer 538 reactor. The advantage of this procedure is that assuming that heat-up speed is equal, the maximum temperature of the product at the output from the Pasteurizer 538 reactor will be lower than in a system having a recuperator 512. The drawback, however, is that the extent of deaeration is reduced.

It is also possible to operate the system without the deaerator 501. In this case, the product is fed into the Pasteurizer 538 reactor immediately through valve 508, while 507 is closed, or through valve 508, valve 505, product pump 506, valve 507, while valve 504 is closed.

If recuperator 512 is not utilized, then there is no need to use product pump 546. In this case the Pasteurized product is discharged from Pasteurizer 538 reactor into the vacuum chamber 532 through valve 545 by the force of gravity.

EXAMPLE 7

Using the reactor shown in FIGS. 14–17 and described in Example 6, the following test was conducted. The reactor system, before operation, was subjected to vacuum conditions by a vacuum water circuit purnp for one hour to remove residual gasses, down to a pressure of 14 kPa. The steam generator was degassed by heating to 69° C. for one hour, and then all portions of the reactor were steamed at a temperature of 75–100° C., with the vacuum pump turned off. After steaming, the condensate was discharged from the tanks, and the reactor and steam generator hermetically sealed. The reactor was then subjected to partial vacuum and cooled down to 69° C. The steam heater was set to 150° C., with the steam generator set to 65° C.

A physiological solution was initially processed by degassing for 45 minutes. This solution was then fed through the reactor at a maximum rate of 50 liters per minute. The initial concentration of *E. coli* bacteria in the solution was $8 \times 10^6$ per ml, the initial temperature 20° C., and initial pHE=5.1. After treatment, the bacteria were reduced to 20% of starting values, the final temperature was 47° C., and final pH=6.1. Nine liters of fluid were treated in 36 seconds, with a consumption rate of 0.9 m$^3$ per hour. The fluid was pressurized under argon with 4 atmospheres pressure. The average saturated steam temperature within the reactor was 60° C.

The fluid tank was filled with a physiological solution containing *E. coli* from a sealed bottle. After fill-up, the physiological solution was evacuated through a vacuum pump for a period of 45 minutes in order to degas the product. Argon was delivered into the source product tank under a positive pressure of 4.0 atmospheres, and the maximum outflow rate, with the control valve being fully open, was established. The duration for discharge of 9 liters of physiological solution was 36 seconds, which corresponds to a consumption rate of 0.9 $m^3$/hr. The initial portion of the processed product, about 1 liter, and the final 1 liter portion were discharged into the drain tank, because the startup and completion periods may induce defects in the treatment or be nonuniformly treated. During the middle portion of the treatment, the product ported into the processed product tank, from which a 0.5 liter sample was taken directly into a hermetically sealed glass vessel.

Upon completion of Pasteurization, the steam generator was turned off, and argon was delivered into the reactor and the product was discharged. After discharge, the system was cleaned with an alkaline solution, followed by rinsing with distilled water. The system was disassembled, examined, subjected to boiling of the disassembled reactor, tanks and removable parts of the vacuum system for 5 hours. After cleaning the surface, the system was reassembled.

Based on an analysis of thermocouple data, it is apparent that heating of the droplets occurs within an interval of 70 mm from the nozzle orifice, with a gradient of 0.55° C. per mm, as shown in FIG. 18B. Due to the high fluid flow rate, and a relative insufficiency of the power of the boiler, the Pasteurization process was non-stationary, as shown by the divergence of P and Ps in FIG. 18A. The steam pressure in the steam generator during the process was lower than the saturation pressure in the steam generator by a factor of 1.0–1.5 kPa. The temperature in the droplet cone was about 60–50° C., i.e. the steam was wet.

As was demonstrated by further tests, wet steam is not conducive to optimal results.

EXAMPLE 8

In order have the system described in FIGS. 14–17 operate in a stationary mode, the following changes were made from the procedure described in Example 7:

(1) The power of the steam generator was increased to 12 BTU, together with a superheater it amounted to 15 BTU.

(2) The centrifugal jet injector, having a nozzle diameter of 4.8 mm, was replaced by a centrifugal jet injector having a nozzle diameter of 2.0 mm, thus reducing flow rate.

(3) The geometry of the steam distributor was changed.

(4) Sample testing was performed using a disposable syringe during Pasteurization.

A test was conducted as follows: Starting conditions: $10^6$ *E. coli* per ml, temperature 21° C., pH=5.37, fluid volume 15 liters. Final conditions: less than 2 *E. coli* per ml, i.e., $2\times10^6$ times the starting amount (the limit of the sensitivity of the detection method), temperature 64° C., pH=6.8. The consumption rate was 150 liters per hour. The steam saturation temperature Ts=65° C., with the temperature of the superheated steam being 77° C.

The tests on the air-tightness of the system before the experiment proved that there was no gas in-leakage. The process was conducted with a temperature in the steam generator being equal to 65° C. The steam in the heater was about 10° C. higher than the saturation temperature. Before injecting the liquid into the reactor, the pumping rate was lowered to such level, so that 10% of the power capacity of the steam generator was expended. When the fluid was injected, the steam generator automatically switched to 100% power mode. The reduced power mode was maintained for 5 min. prior to commencing treatment.

Under these conditions, a stationary mode of operation was achieved for 250 seconds, as shown in FIG. 19A. The difference between pressure in the reactor P and the saturation pressure Ps did not exceed 100 Pa. The temperature gradient at the surface of the cone was 2° C. per mm, as shown in FIG. 19B.

EXAMPLE 9

Further tests pertaining to *B. subtilis* and milk were performed in a manner similar to that set forth in Examples 7 and 8.

The following method was conducted:

(1) preliminary vacuum treatment of reactor was conducted for one hour.

(2) gas in-leakage was tested using pressure sensors (gas in-leakage tolerance was approved for no more than 100 Pa during 6 minutes, the duration of the test).

(3) parts of the reactor were steamed with superheated steam having a temperature of 100–150° C. for 30 minutes.

(4) condensate was discharged.

(5) The raw product was vacuum pumped into the tank for a duration of 5 minutes.

(6) The raw product was treated in the reactor and test samples drawn.

(7) The equipment was cleaned.

The tests were conducted under different conditions with respect to vacuum level and gas in-leakage.

*B. subtilis* was present at a starting concentration $8 \times 10^4$ per ml, initial liquid temperature 20° C., initial pH=6.67, volume of solution equal to 15 liters. *B. subtilis* final concentration 0.23–0.28% of original concentration, final temperature 66° C., final pH=6.67, consumption rate 150 liters per hour. The saturation temperature Ts was 67° C., and the temperature of the superheated steam was 130–115° C. The degassing of the steam generator was conducted at a power equal to about 30% of the actual power of the steam generator.

Figure 20A:
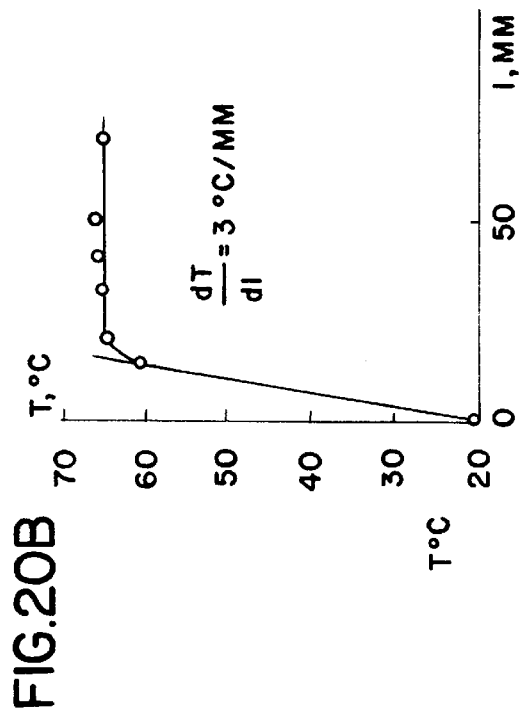
Figure 20B:
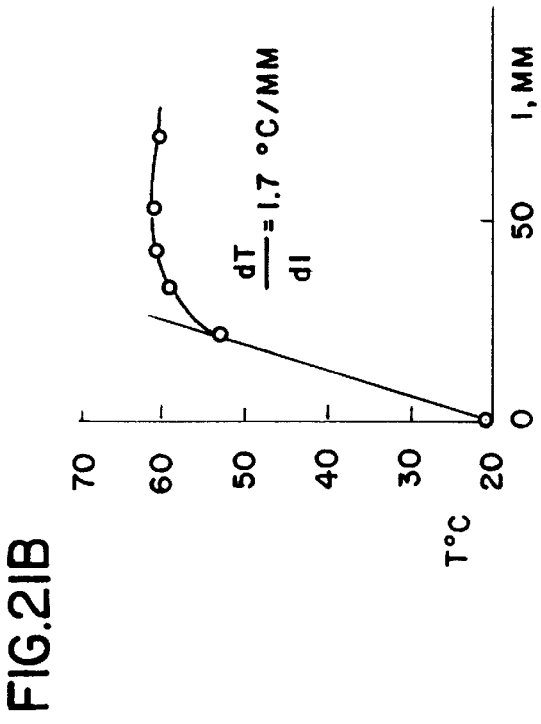

Under these circumstances, the steam pressure P varied over time, as well as the saturation pressure Ps. The process was not stationary, as shown in FIG. 20A, and the steam was wet, with a Ps-P of about 1.5 kPa. The results are therefore similar to those obtained for Example 6, and the remaining amount of active bacteria is approximately 25% of starting values, even with a relatively high temperature gradient of 3° C. per mm, as shown in FIG. 20B.

EXAMPLE 10

Using a method similar to that of Example 9, the following results were obtained. A starting concentration of $10^4$ per ml of *E. coli* and milk microflora in milk was measured. The initial temperature was 20°, initial pH=6.67, with a volume of 15 liters.

The system produced a reduction to 2%, 1.5% and 3% of starting bacterial concentrations, with a final temperature of 60.5° C., final pH=6.87, and a consumption rate of 150 liters per hour. The saturation temperature Ts was 62° C., with the temperature of the superheated steam being between 170–115° C.

Figure 21A:
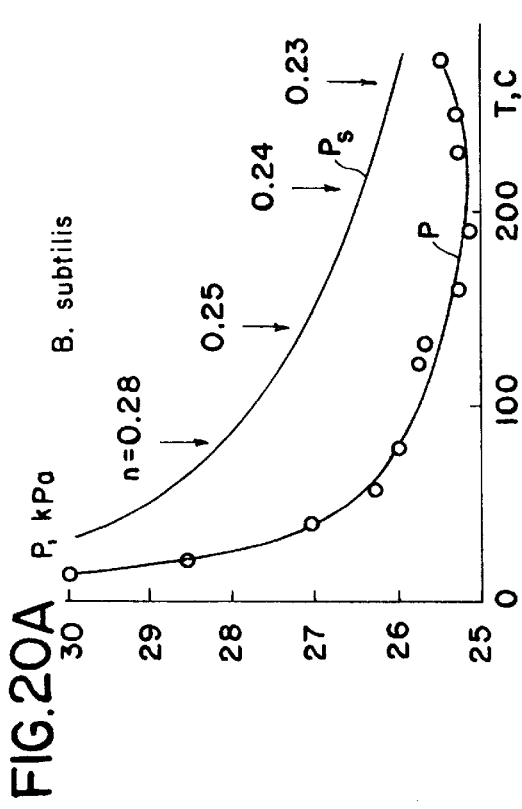

During Pasteurization process, there is a simultaneous increase of pressure in the Pasteurizer P and the steam generator Ps, indicating that gases are emitted from the liquid that is undergoing Pasteurization. Due to the low throughput, which corresponded to approximately to 7% of the actual power capacity of the steam generator, and to the high content of gases in the milk, there is a great increase of non-condensing gases in the reactor, reaching a pressure P of 2.5 kPa, as shown in FIG. 21A. FIG. 21A also shows that the process was initially stationary, and later, at about 180 seconds, became progressively non-stationary, until the process was almost over. All these factors result in reduced efficacy. Further, the initial temperature of the milk was 20° C., at which temperature fat globules are solid, probably contributing to the negative effect, though the non-condensing gasses are primarily responsible for the failure to achieve sterilization.

Figure 21B:
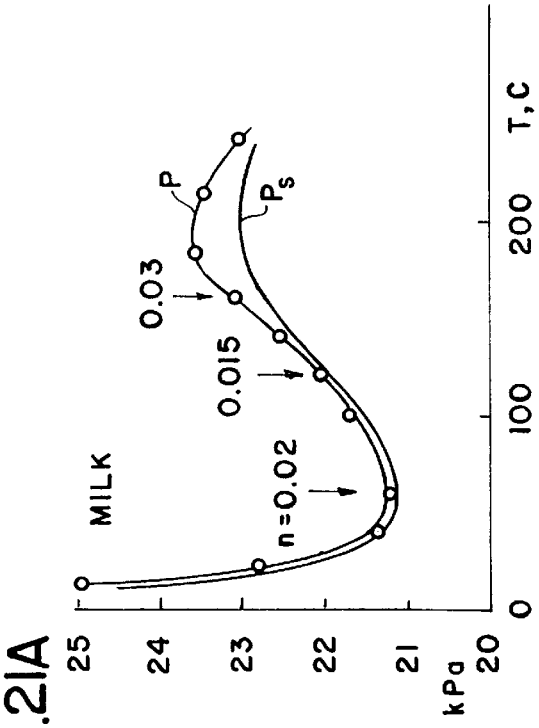

The temperature gradient was 1.7° C. per mm, as shown in FIG. 21B.

In a prior study, milk containing *E. coli* and the microflora of about $10^5$ per ml underwent steam heating in an identical process, starting at T=21° C. and being raised to 62° C., which produced complete killing of *E coli*, down to less than about $2 \times 10^{-5}$ per ml. That test was conducted on one liter of milk which was injected into a 60 liter reactor during 3 seconds, without vacuum, i.e. in a stationary mode with a negligible pressure variation in the reactor due to release of the gases dissolved in the milk.

Therefore, it can be seen that the rate of withdrawal of non-condensing gases in liquid undergoing steam processing is an important feature of the process. When the speed of withdrawal is low, gas is collected in the reactor, and the amount of steam which condenses on the milk droplets is reduced. However, when the speed of withdrawal is high, steam becomes wet, and this significantly deteriorates the efficacy of the process.

The best results are obtained in a hermetically sealed unit using dry saturated steam. Preliminary degassing of the milk reduces the outgassing problem.

EXAMPLE 11

Figure 15:
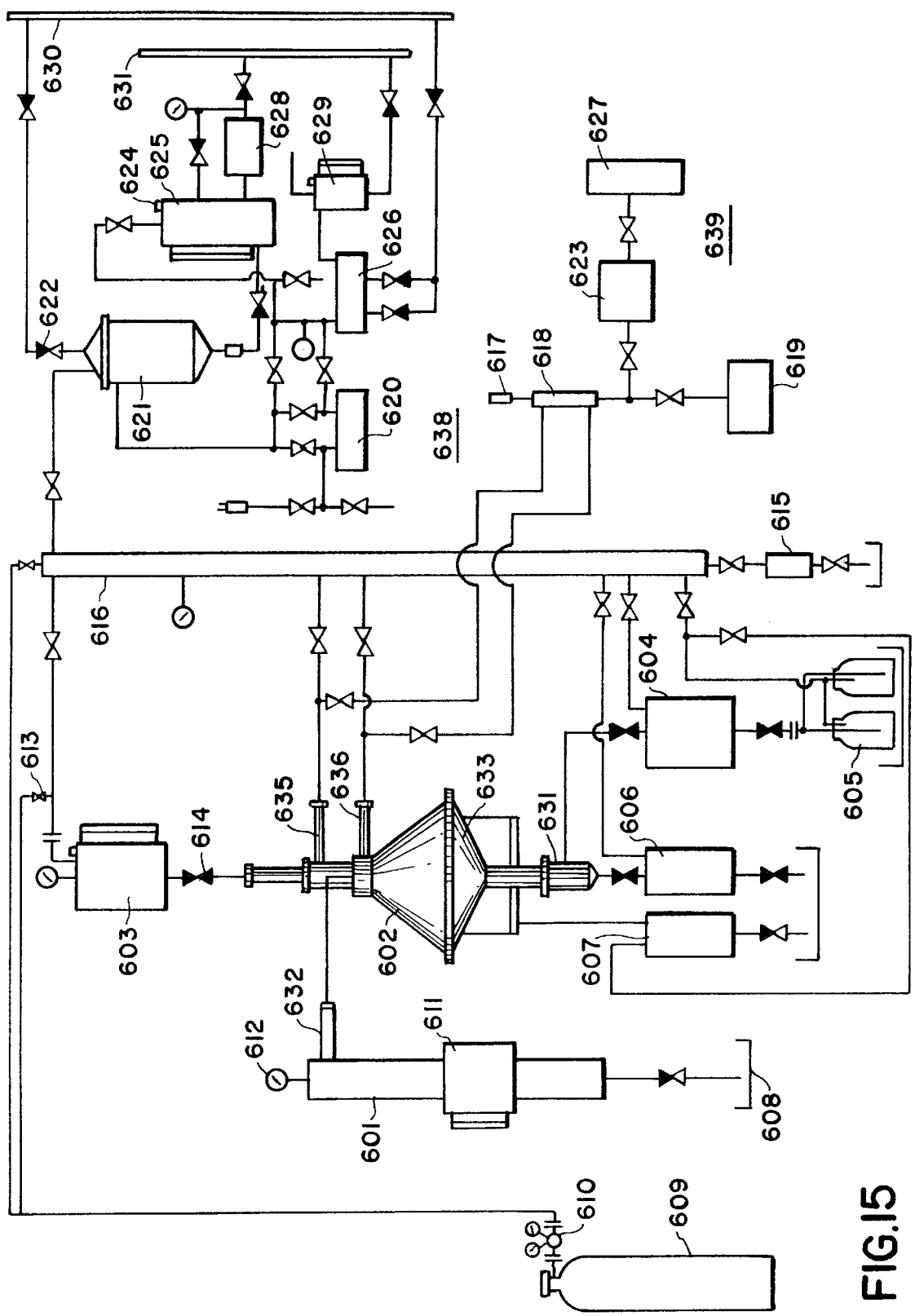
Figure 17A:
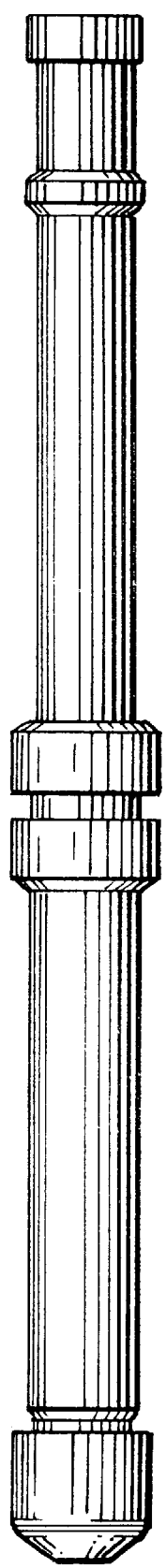
FIGS. 17A and 17B show an elevation and cross section view of an injection nozzle according to the present invention.
Figure 17B:
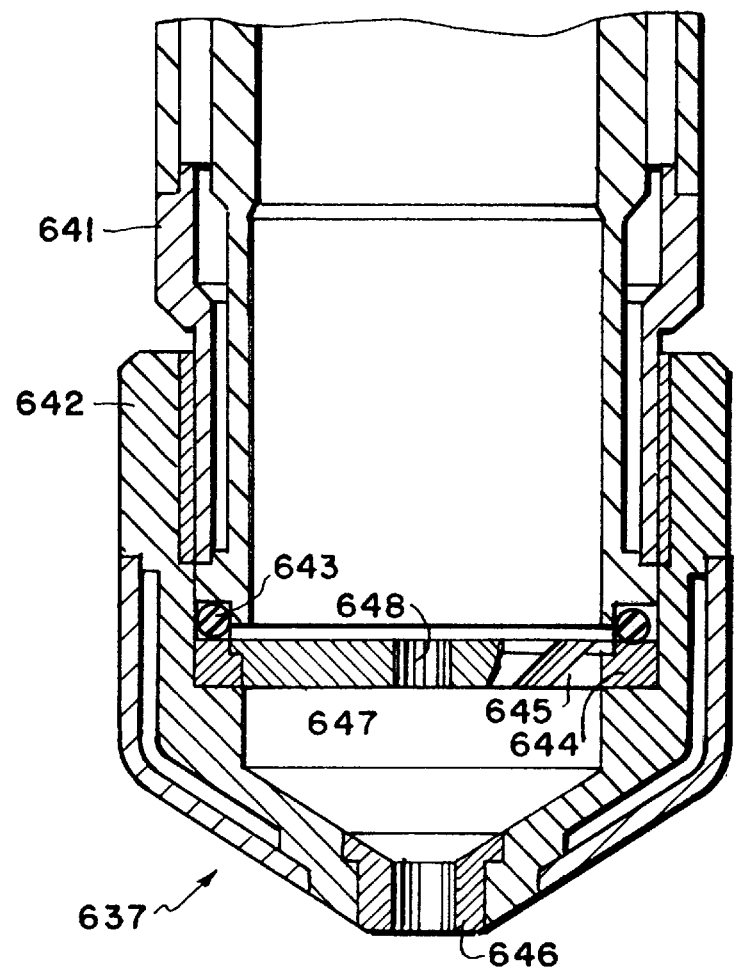
Figure 18B:
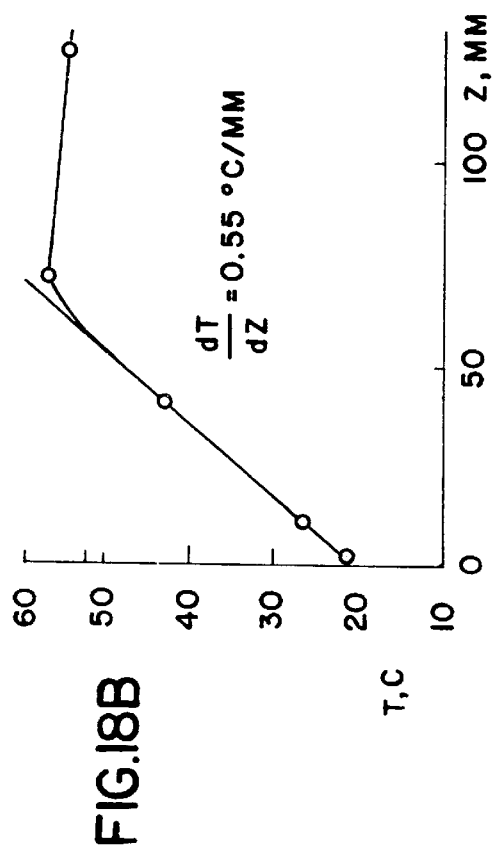
FIGS. 18A, 18B, 19A, 19B, 20A, 20B, 21A and 21B show time-pressure and distance-temperature relationships, respectively, during operation of the Pasteurization reactor according to the present invention.
Figure 18A:
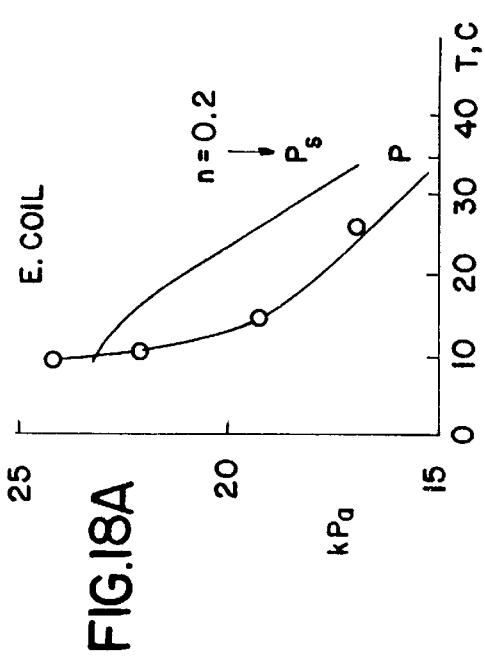
Figure 19B:
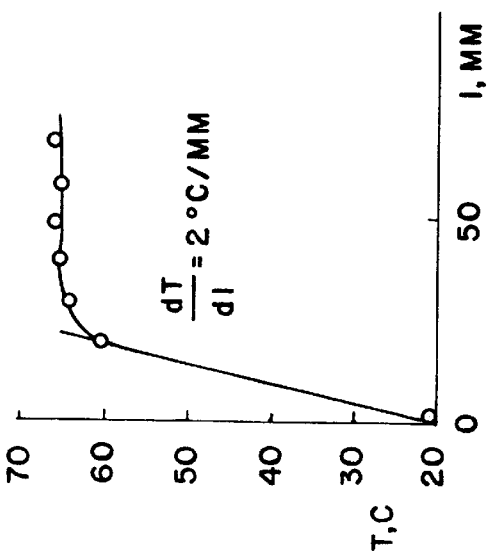
Figure 19A:
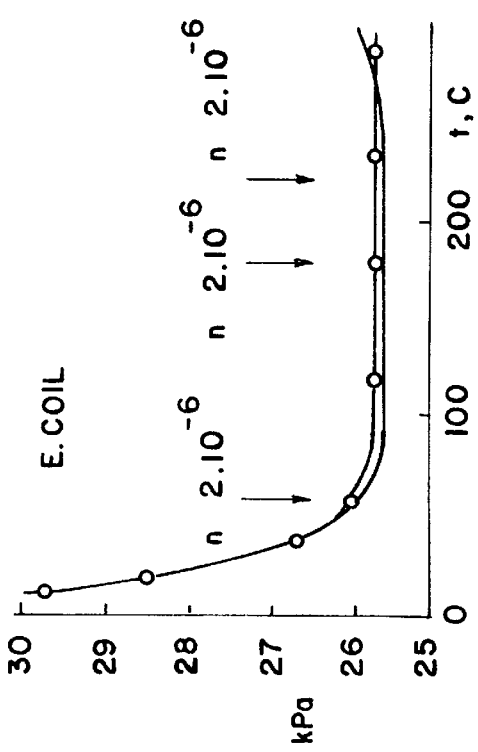

The apparatus as shown in FIGS. 14 and 15 are used to Pasteurize beer. The initial temperature is 4° C., with a final temperature of 40° C. The beer is degassed to 50 mm Hg prior to treatment, and recharged with carbon dioxide gas, after treatment and cooling. For a standard product, the steam includes about 4% ethanol, to maintain alcohol level. For a low alcohol product, steam without ethanol is employed. Low alcohol products are further subjected to flash cooling and alcohol removal under vacuum after processing. The resulting product may be filtered to remove sediment.

EXAMPLE 12

A standard blood pheresis apparatus, available from Johnson & Johnson, is employed in an extracorporeal reactor system to remove and separate blood components. The leukocyte-rich fraction is diluted 1:10 in degassed 4° C. normal saline, and passed through a reactor similar to that shown in FIGS. 14 and 15, although smaller. For example, the reactor is 120 mm high. Droplets are atomized as 75–100 microns. Steam is injected into the reactor to reach a maximum temperature of 35–40° C. flow through the reactor is about 100 ml per minute. The processed leukocytes are reinfused into the patient. Fluid overload is limited by retaining plasma from the pheresis system, as necessary (which may be reinfused later), and limiting the duration of the treatment. Leukocytes may also be concentrated from the treated stream and excess fluid eliminated.

This treatment may be used to treat blood borne diseases, immunological disorders and syndromes, AIDS, CFS, viral diseases, leukemias and blood disorders.

EXAMPLE 13

The apparatus as shown in FIGS. 14 and 15 is used to process bacterial, fungal or cell culture medium. The cells are initially provided at a temperature of 4–45° C., depending on type. The medium is initially degassed to 50–100 mm Hg non-condensing gasses, with most of the remaining gas as oxygen, unless the culture is anaerobic. A mild, non-lethal treatment provides a temperature rise of about 2–15° C., while a lethal treatment provides a temperature rise of about 15–50° C. Temperature rise rate may be controlled as well, with larger rates being stronger treatments.

EXAMPLE 14

A skin treatment device is provided. The effected areas are separated from the environment by an enclosure, having uniformly spaced steam vents. The enclosure is evacuated to a vacuum of about 0.5 atmospheres, with noncondensing gasses replaced with water vapor. A soft gasket material rests against the skin at the periphery of the region to be treated. The treatment consists of the rapid infusion of steam at about 50° C. into the vacuum space, directed at the skin. The steam treatment operation lasts less than 0.25 second, and may be repeated. The conditions of the treatment are controlled to prevent tissue burning and mass necrosis.

It should be understood that the preferred embodiments and examples described herein are for illustrative purposes only and are not to be construed as limiting the scope of the present invention, which is properly delineated only in the appended claims.

What is claimed is:

1. A method for treating at least one cell of a biological organism in a medium with a thermal shock so as to alter processes within said cell, the cell having at least one membrane, and wherein the medium or the cell have biological proteins, comprising heating the medium containing the cell by a temperature of at least about 2° C. at a rate which exceeds a relaxation rate of said at least one membrane of the at least one cell, under such time and temperature conditions which do not thermally denature a substantial portion of the biological proteins, and substantially without immediately killing the at least one cell.

2. The method according to claim 1, wherein the temperature rise is at least 5° C.

3. The method according to claim 1, wherein the temperature rise is at least 10° C.

4. The method according to claim 1, wherein the temperature rise rate is at least 1000° C. per second.

5. The method according to claim 1, wherein the temperature rise rate is at least 2000° C. per second.

6. The method according to claim 1, wherein the maximum temperature is below about 55° C.

7. The method according to claim 1, wherein the maximum temperature is below about 45° C.

8. The method according to claim 1, wherein the maximum time temperature product of the heating process is less than about 200° C. ● seconds over an integation period of five seconds.

9. The method according to claim 1, wherein the heating is effected through condensation of steam.

10. The method according to claim 1, wherein the medium has a partial pressure of non-condensing gasses of less than about 150 mm Hg prior to heating.

11. The method according to claim 1, wherein the at least one cell is a genetically engineered cell.

12. The method according to claim 1, wherein the at least one cell is a neoplastic cell.

13. The method according to claim 1, wherein the at least one cell is a leukocyte.

14. The method according to claim 1, wherein the at least one cell contains viral genetic material.

15. The method according to claim 1, wherein the heating is effected by condensation of dry steam at subatmospheric pressure on droplets of medium.

16. The method according to claim 1, wherein the heating effects a treatment substantially without killing the at least one cell.

17. The method according to claim 1, wherein the at least one cell is contained in a droplet less than about 0.3 mm diameter.

18. The method according to claim 1, wherein the at least one cell is heated with microwave radiation.

19. The method according to claim 1, wherein the at least one cell is heated with laser radiation.

20. The method according to claim 1, wherein the at least one cell is heated with infrared radiation.

21. The method according to claim 1, wherein the at least one cell is treated while in the organism.

22. A method for treating at least one cell of a biological organism in a medium with a thermal shock so as to alter processes within said cell and introducing said cell into an organism after the treatment, and wherein the medium or the cell have biological proteins, comprising heating the medium containing the cell by a temperature of at least about 2° C. at a rate which exceeds a relaxation rate of said at least one membrane of the at least one cell, under such time and temperature conditions which do not thermally denature a substantial portion of the biological proteins, and substantially without immediately killing the at least one cell, and introducing the at least one treated cell into an organism after heating.

23. The method according to claim 22, wherein the at least one cell is of a type which normally circulates in the blood, further comprising the step of separating the at least one cell from blood cells of differing types before heating.

\* \* \* \* \*